US006030720A

United States Patent [19]
Chu et al.

[11] Patent Number: 6,030,720
[45] Date of Patent: Feb. 29, 2000

[54] LIQUID ELECTROLYTE LITHIUM-SULFUR BATTERIES

[75] Inventors: May-Ying Chu, Oakland; Lutgard C. De Jonghe, Lafayette; Steven J. Visco, Berkeley; Bruce D. Katz, Oakland, all of Calif.

[73] Assignee: PolyPlus Battery Co., Inc., Berkeley, Calif.

[21] Appl. No.: 08/948,969

[22] Filed: Oct. 10, 1997

Related U.S. Application Data

[63] Continuation-in-part of application No. 08/686,609, Jul. 26, 1996, Pat. No. 5,686,201, which is a continuation-in-part of application No. 08/479,687, Jun. 7, 1995, Pat. No. 5,582,623, which is a continuation-in-part of application No. 08/344,384, Nov. 23, 1994, Pat. No. 5,523,179.

[51] Int. Cl.[7] .................................................. H01M 10/40
[52] U.S. Cl. ......................... 429/105; 429/325; 429/328; 429/329; 429/337; 429/339
[58] Field of Search .................................... 429/105, 325, 429/328, 329, 337, 339

[56] References Cited

U.S. PATENT DOCUMENTS

| | | | |
|---|---|---|---|
| 3,404,035 | 10/1968 | Kummer et al. | 136/6 |
| 3,413,150 | 11/1968 | Kummer et al. | 136/6 |
| 3,532,543 | 10/1970 | Nole et al. | 136/6 |
| 3,806,369 | 4/1974 | Dey et al. | 429/339 X |
| 3,907,591 | 9/1975 | Lauck | 136/6 |
| 3,915,743 | 10/1975 | Lauck | 136/6 |
| 3,953,231 | 4/1976 | Farrington et al. | 136/6 |
| 4,008,357 | 2/1977 | Nishimura et al. | 429/339 X |
| 4,132,837 | 1/1979 | Soffer | 429/329 X |
| 4,143,214 | 3/1979 | Chang . | |
| 4,268,587 | 5/1981 | Farrington et al. | 429/193 |
| 4,410,609 | 10/1983 | Peled et al. | 429/105 |
| 4,469,761 | 9/1984 | Bennett et al. | 429/50 |
| 4,644,911 | 2/1987 | Perichaud et al. | 429/194 |
| 4,833,048 | 5/1989 | Dejonghe et al. | 429/104 |
| 4,917,974 | 4/1990 | De Jonghe et al. | 429/104 |
| 5,130,211 | 7/1992 | Wilkinson et al. | 429/337 X |

(List continued on next page.)

FOREIGN PATENT DOCUMENTS

| | | |
|---|---|---|
| 0602984A2 | 6/1994 | European Pat. Off. . |
| 2.124.388 | 9/1972 | France ........................... H01M 21/00 |
| 6-275313 | 9/1994 | Japan ............................. H01M 10/36 |
| 2.084.391 | 4/1982 | United Kingdom ............ H01M 6/16 |
| 2 273 603A | 10/1984 | United Kingdom . |
| 2 137406A | 6/1994 | United Kingdom . |

OTHER PUBLICATIONS

Toshiba, S., et al., "Study on the reduction species of sulfur by alkali metals in nonaqueous solvents", *Electrochimica Acta*, vol., 42, No. 6, 1997, pp. 1019–1029, XP004016985. (Month Unknown).

(List continued on next page.)

*Primary Examiner*—Stephen Kalafut
*Attorney, Agent, or Firm*—Beyer & Weaver, LLP

[57] ABSTRACT

Disclosed are electrolyte solvents for ambient-temperature lithium-sulfur batteries. The disclosed solvents include at least one ethoxy repeating unit compound of the general formula $R_1(CH_2CH_2O)_nR_2$, where n ranges between 2 and 10 and $R_1$ and $R_2$ are different or identical alkyl or alkoxy groups (including substituted alkyl or alkoxy groups). Alternatively, $R_1$ and $R_2$ may together with $(CH_2CH_2O)_n$ form a closed ring. Examples of linear solvents include the glymes $(CH_3O(CH_2CH_2)_nCH_3)$. Some electrolyte solvents include a donor or acceptor solvent in addition to an ethoxy compound as described. Examples of donor solvents include hexamethylphosphoramide, pyridine, N,N-diethylacetamide, N,N-diethylformamide, dimethylsulfoxide, tetramethylurea, N,N-dimethylacetamide, N,N-dimethylformamide, tributylphosphate, trimethylphosphate, N,N,N',N'-tetraethylsulfamide, tetramethylenediamine, tetramethylpropylenediamine, and pentamethyldiethylenetriamine. These assist in solvation of lithium ions. Examples of acceptor solvents include alcohols, glycols, and polyglycols. These assist in solvation of the sulfide and polysulfide anions.

49 Claims, 12 Drawing Sheets

U.S. PATENT DOCUMENTS

| | | | |
|---|---|---|---|
| 5,162,175 | 11/1992 | Visco et al. | 429/192 |
| 5,506,072 | 4/1996 | Griffin et al. | 429/337 X |
| 5,523,179 | 6/1996 | Chu | 429/104 |
| 5,529,860 | 6/1996 | Skotheim et al. | 429/213 |
| 5,712,057 | 1/1998 | Fauteux | 429/105 |

OTHER PUBLICATIONS

Abstract of proceedings of the 6th International Symposium on Power Sources 2, 1968, Brighton, Sussex, UK, Sep. 24–26, 1968.

Coleman et al., "The Sulfur Electrode" proceedings of the 6th International Symposium on Power sources, pp. 289–302 (1968). (Month Unknown).

Visco, S.J., Liu, M., Armand, B. and De Jonghe, L.C., Solid Redox Polymerization Electrodes and Their use in All–Solid–State Batteries, Mol. Cryst. Liq. Cryst., 190, p. 198, 1990. (Month Unknown).

Societe des Accumulateurs Fixes et de Traction, "Lithium–sulfer battery" Abstracts 111055d, Chemical Abstracts 66: 10360; 1967, (Month Unknown).

DeGott, P., "Polymere Carbone–Soufre Synthese Et Proprietes Electrochimiques," Doctoral Thesis at l'Institut National Polytechnique de Grenoble, (Date of Defense Jun. 19, 1986).

Lauck, H., "Storage battery with lithium anode and sulfur cathode," Abstract # 9855s, Chemical Abstracts, 80: 467–468; 1974. (Month Unknown).

Peled et al., Rechargeable Lithium–Sulfur Battery (Extended Abstract), Journal of Power Source, 26: 269–271, 1989. (Month Unknown).

Peled et al.; "Lithium–Sulfur Battery: Evaluation of Dioxolane–Based Electrolytes", J. Electrochem., Soc., 136 (6): 1621–1624, Jun. 1989.

Peramunage and Licht, "A Solid Sulfer Cathode for Aqueous Batteries"; Science 261: 1029–1032, Aug. 20, 1993.

Rauth et al., "Formation of Lithium Polysulfides in Aprotic Media", J. Inorg., Nuc. Chem., 39: 1761–1765, 1977. (Month Unknown).

Rauh et al. "A Lithium/Dissolved Sulfur Battery with an Organic Electrolyte"; J. Electrochem. Soc., 126(4): 523–527, Apr. 1979.

Yamin and Peled, "Electrochemistry of Nonaqueous Lithium/Sulfur Cell", J. Power Sources, 9: 281–287, 1983. (Month Unknown).

Yamin et al., Lithium Sulfur Battery,: J. Electrochem. Soc., 135(5): 1045–1048, May 1988.

S.J. Visco, M.M. Doeff, and L.C. De Jonghe, "Thin–Film Technology for Solid–State Lithium Batteries Employing Solid Redox Poly–Merization Cathodes", pp. 89–92, Society of Vacuum Coaters, 1991. (Month Unknown).

Liu, Meilin, Visco, Steven J., and De Jonghe, Lutgard C., "Novel Solid Redox Polymerization Electrodes Electrochemical Properties", J. Electrochem Soc., vol. 138, No. 7, pp. 1896–1901, Jul. 1991.

Liu, Meilin, Visco, Steven J., and De Jonghe, Lutgard C., "Novel Solid Redox Polymerization Electrodes All–Solid State, Thin–Film, Rechargeable Lithium Batteries", J. Electrochem Soc., vol. 138, No. 7, pp. 1891–1895, Jul. 1991.

Ue, Makoto, Visco, Steven J., and De Jonghe, Lutgard C., "Comparison of Cathode Utilization between Polymeric Organodisulfide and Titanium Disulfide in Solid Polymer Electrode Rechargeable Lithium Cells", Denki Kagaku, vol. 61, No. 12, pp. 1409–1415, 1993. (Month Unknown).

Meilin, Lui, "Novel Electrodes for Advanced Energy Storage System" Dissertation for Ph.D. at the University of Berkeley, Chapter 2, pp. 3–6, 1989. (Month Unknown).

R.D. Rauh, et al., Rechargeability Studies of Ambient Temperature Lithium/Sulfur Batteries, EIC Corporation, 55 Chapel Street, Newton, MA 02158. (1977) (Month Unknown).

E. Peled, et al. "Lithium–Sulfur Battery: Evaluation of Dioxolane Based Electrodes", J. Electrochemical Society, 136, 1621–1624 (1989). (Month Unknown).

A. Yamin, et al. "Electrochemistry of a Nonaqueous Lithium/Sulfur Cell", J. Power Sources, 9, 281–287 (1983). (Month Unknown).

H. Yamin, et al. "Lithium Sulfur Battery –Oxidation/Reduction Mechanisms of Polysulfides in THF Solutions", J. Electrochemical Society, 135, 1045–1048 (1988). (May).

S.B. Brummer, et al. "Low Temperature Lithium/Sulfur Secondary Battery", U.S. Energy Research and Development Administration Div. of Electric Energy Systems, 1–57, (1976). (Month Unknown).

E. Peled, et al. "Rechargeable Lithium–Sulfur Battery (Extended Abstract)", J. Power Sources, 26, 269–271 (1989). (Month Unknown).

Kavan, L., Novak, P., and Dousek, F.P., "Electrochimica Acto," vol. 33, No. 11, pp. 1605–1612, Mar. 8, 1988, Great Britain.

Brummer, S.B., et al., "Low Temperature Lithium/Sulfur Secondary Battery (Annual Progress Report, Dec. 1, 1974–Dec. 1, 1975)," EIC Corporation, Apr. 1976, Newton, Massachusetts.

Larry A. Dominey, "Lithium Batteries" New Materials, Developments and Perspectives, 1994, New York, Industrial Chemistry Library, vol. 5, pp. 137–165. (Month Unknown).

Ronald Snaith, et al., "Lithium Chemistry" A Theoretical and Experimental Overview, 1995, New York, John Wiley & Sons, Inc., pp. 227–47. (Month Unknown).

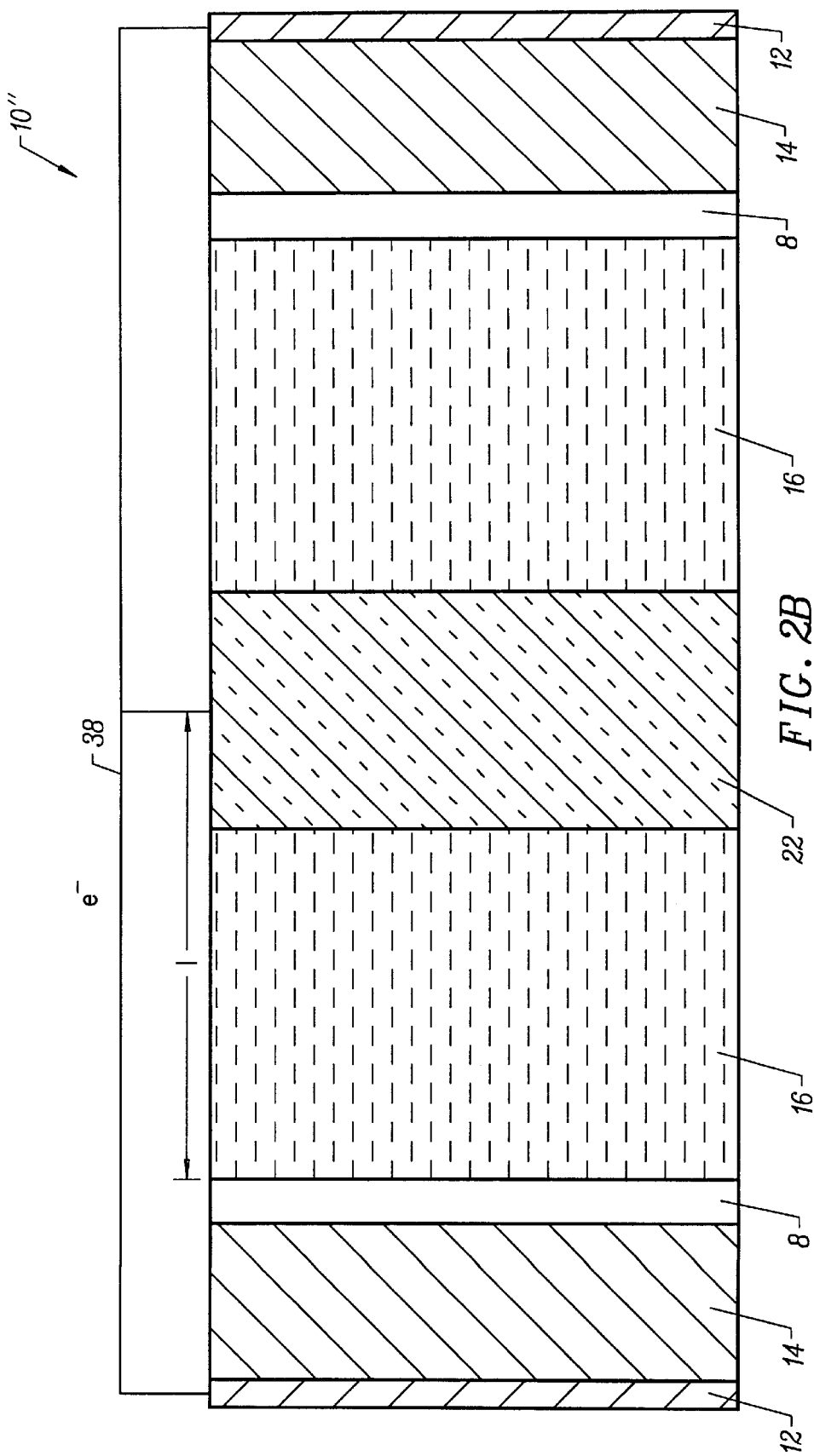

| | electronically conductive material | wt% | binding agent | wt% | dispersing agent | wt% | active sulfur | wt% | electrolyte salt | wt% | liquid solvent | wt ratio of liquids to solids |
|---|---|---|---|---|---|---|---|---|---|---|---|---|
| slurry#1 | acetylene black (Chevron) | 24% | PEO, Mw=900k (Aldrich) | 20% | Brij 35 (Aldrich) | 2% | elemental (sublimed from Aldrich) | 50% | Li-tri-flouromethane sulfonimide. (HQ-155, 3M Company) | 4% | Acetonitrile | 50:1 |
| slurry#2 | acetylene black (Chevron) | 10% | PEO, Mw=900k (Aldrich) | 20% | Brij 35 (Aldrich) | 5% | elemental (sublimed from Aldrich) | 65% | none | NA | Acetonitrile | 20:1 |
| slurry#3 | acetylene black (Chevron) | 28% | PEO, Mw=900k (Aldrich) | 20% | Brij 35 (Aldrich) | 2% | elemental (sublimed from Aldrich) | 50% | none | NA | Acetonitrile | 20:1 |
| slurry#4 | acetylene black (Chevron) | 70% | PEO, Mw=900k (Aldrich) | 25% | Brij 35 (Aldrich) | 5% | none | NA | none | NA | Acetonitrile | 20:1 |
| slurry#5 | graphite flake (Asbury Graphite) | 70% | PEO, Mw=900k (Aldrich) | 25% | Brij 35 (Aldrich) | 5% | none | NA | none | NA | Acetonitrile | 20:1 |
| slurry#6 | XC-72 (Cabot) | 70% | PEO, Mw=900k (Aldrich) | 25% | Brij 35 (Aldrich) | 5% | none | NA | none | NA | Acetonitrile | 20:1 |
| slurry#7 | acetylene black (Chevron) | 80% | Teflon™ (DuPont Company) | 20% | none | NA | none | NA | none | NA | Isopropyl alcohol | 30:1 |

FIG. 3B

| Example | maximum % utilization | % utilization during cycles | Number of Cycles | discharge rate mA/cm² |
|---|---|---|---|---|
| 1 | 11% | 11% | 600+ | ~0.1 |
| 2 | ~55% | ~40% | 70+ | ~0.1 |
| 3 | ~50% | ~40% | 70+ | 0.5 |
| 4 | 65% | ~60% | 35+ | ~0.1 |
| 5 | ~35% | ~30% | 30+ | 1.0 |
| 6 | 50% | ~40% | 50+ | 0.5 |

FIG. 4

FIG. 5 End of discharge voltage vs number of recharge cycles (11 % Sulfur Utilization, 25°C)

FIG. 6 Percent Sulfur Utilization vs. number of recharge cycles (25°C)

FIG. 7  Percent Sulfur Utilization vs. number of recharge cycles (25°C)

FIG. 8 Percent Sulfur Utilization vs. number of recharge cycles (25°C)

FIG. 9  Percent Sulfur Utilization vs. number of recharge cycles (25°C)

LIQUID ELECTROLYTE LITHIUM-SULFUR BATTERIES

CROSS-REFERENCE TO RELATED APPLICATIONS

This application is a continuation-in-part of U.S. patent application Ser. No. 08/686,609, filed Jul. 26, 1996, and entitled RECHARGEABLE POSITIVE ELECTRODES, now U.S. Pat. No. 5,686,201, which is a continuation-in-part of U.S. patent application Ser. No. 08/479,687 (now U.S. Pat. No. 5,582,623, issued Dec. 10, 1996, filed June 7, 1995, and entitled METHODS OF FABRICATING RECHARGEABLE POSITIVE ELECTRODES) which is, in turn, a continuation-in-part of U.S. patent application Ser. No. 08/344,384 (now U.S. Pat. No. 5,523,179, issued Jun. 4, 1996, filed Nov. 23, 1994, and entitled RECHARGEABLE POSITIVE ELECTRODE). U.S. Pat. No. 5,686,201 is incorporated herein by reference for all purposes. In addition, both U.S. Pat. Nos. 5,582,623 and 5,523,179 are incorporated herein by reference for all purposes.

BACKGROUND OF THE INVENTION

This invention relates to liquid electrolyte compositions and cell configurations for metal-sulfur batteries (e.g., lithium-sulfur batteries).

The rapid proliferation of portable electronic devices in the international marketplace has led to a corresponding increase in the demand for advanced secondary batteries (i.e., rechargeable batteries). The miniaturization of such devices as, for example, cellular phones, laptop computers, etc., has naturally fueled the desire for rechargeable batteries having high specific energies (light weight). At the same time, mounting concerns regarding the environmental impact of throwaway technologies, has caused a discernible shift away from primary batteries and towards rechargeable systems.

In addition, heightened awareness concerning toxic waste has motivated, in part, efforts to replace toxic cadmium electrodes in nickel/cadmium batteries with the more benign hydrogen storage electrodes in nickel/metal hydride cells. For the above reasons, there is a strong market potential for environmentally benign secondary battery technologies.

Secondary batteries are in widespread use in modern society, particularly in applications where large amounts of energy are not required. However, it is desirable to use batteries in applications requiring considerable power, and much effort has been expended in developing batteries suitable for high specific energy, medium power applications, such as, for electric vehicles and load leveling. Of course, such batteries would also be suitable for use in lower power applications such as cameras or portable recording devices.

At this time, the most common secondary batteries are probably the lead-acid batteries used in automobiles. Those batteries have the advantage of being capable of operating for many charge cycles without significant loss of performance. However, such batteries have a low energy to weight ratio. Similar limitations are found in most other systems, such as Ni—Cd and nickel metal hydride systems.

Among the factors leading to the successful development of high specific energy batteries, is the fundamental need for high cell voltage and low equivalent weight electrode materials. Electrode materials must also fulfill the basic electrochemical requirements of sufficient electronic and ionic conductivity, high reversibility of the oxidation/reduction reaction, as well as excellent thermal and chemical stability within the temperature range for a particular application. Importantly, the electrode materials must be reasonably inexpensive, widely available, non-explosive, non-toxic, and easy to process.

Thus, a smaller, lighter, cheaper, non-toxic battery is sought for the next generation of batteries. The low equivalent weight of lithium renders it attractive as a battery electrode component for improving weight ratios. Lithium also provides greater energy per volume than do the traditional battery standards, nickel and cadmium.

The low equivalent weight and low cost of sulfur and its nontoxicity renders it also an attractive candidate battery component. Successful lithium/organosulfur battery cells are known. (See, De Jonghe et al., U.S. Pat. Nos. 4,833,048 and 4,917,974; and Visco et al., U.S. Pat. No. 5,162,175.)

Recent developments in ambient-temperature sulfur electrode technology may provide commercially viable rechargeable lithium-sulfur batteries. Chu and colleagues are largely responsible for these developments which are described in the above-referenced U.S. Pat. Nos. 5,582,623 and 5,523,179 (issued to Chu). These developments allow electrochemical utilization of elemental sulfur at levels of 50% and higher over multiple cycles. Because sulfur has a theoretical maximum capacity of 1675 mAh/g (assuming all sulfur atoms in an electrode are fully reduced during discharge), the utilization of sulfur in lithium-sulfur cells as described in the above Chu patents typically exceeds 800 milliamp-hours per gram (mAh/g) of sulfur. Chu's initial work focused on solid and gel-state batteries in which a solid or gel-state ionic conductor was immobilized with the sulfur in an electrode.

Prior to Chu's work, rechargeable ambient-temperature lithium-sulfur batteries were not considered commercially viable. The limited research that was conducted in the field almost universally employed liquid electrolytes which served not only as ionic transport media between the anode and cathode, but also as ionic conductors within the sulfur electrode. Without exception, these electrodes suffered from poor utilization of the sulfur electrode over repeated cycling. For example, one of the best reported rechargeable lithium-sulfur liquid electrolyte batteries cycled 120 times, but had a maximum sulfur utilization of only 5%. See Rauh, R. D., Pearson, G. F. and Brummer, S. B., "Rechageability Studies of Ambient Temperature Lithium/Sulfur Batteries", $12^{TH}$ IECEC, 283–287 (1977). Other rechargeable systems had higher sulfur utilizations, but unacceptably low cycle lives. For example, one group reports a maximum sulfur utilization of about 45%, but their cell was dead by 50 cycles and, during cycling, had a utilization of only about 25%. See Peled, E., Gorenshtein, A., Segal, M., Sternberg, Y., "Rechargeable Lithium-Sulfur Battery (Extended Abstract)", J. Power Sources, 26, 269–271, (1989). Because of their poor cycling performance, the vast majority of prior lithium-battery systems were at best deemed suitable only as primary batteries. In addition, some researchers have concluded that liquid electrolyte/sulfur cells will be intrinsic limited to poor performance. See Coleman, J. R. and Bates, M. W., "The Sulfur Electrode", 289–302 (1968)

It now appears that the poor performance of the prior art lithium-sulfur cells resulted from various design flaws. For example, many cells employed large reservoirs of liquid electrolyte in which sulfide and polysulfide discharge products dissolved, diffused away from the positive electrode, and became unavailable for further electrochemical reaction, thereby reducing the cell's capacity. In addition, it is likely that the prior art cells were operated under conditions in which their discharge products were irreversibly precipitated out of solution, thereby reducing capacity.

Most previously studied liquid electrolyte lithium-sulfur systems employed the same nonaqueous liquid electrolytes that were and are conventionally employed in other lithium-based battery systems (which do not employ sulfur positive electrodes). Such electrolytes generally are designed for maximum conductivity. Typically, they employ low molecular weight solvents such as tetrahydrofuran ("THF"), ethylene carbonate, and/or dimethoxyethane ("glyme") containing high concentrations of lithium salts. Examples of such electrolytes are extensively reviewed in the book "Lithium Batteries, New Materials, Developments and Perspectives," G. Pistoia Ed., Elsevier, New York (1994). See particularly Chapter 4, "Current State of the Art on Lithium Battery Electrolytes." by L. A. Dorniney which is incorporated herein by reference for all purposes. A specific list of such electrolytes is presented in U.S. Pat. No. 3,532,543 issued to Nole et al.

Other references to lithium-sulfur battery systems in liquid formats include the following: Yamin et al., "Lithium Sulfur Battery," *J. Electrochem. Soc.*, 135(5): 1045 (May 1988); Yamin and Peled, "Electrochemistry of a Nonaqueous Lithium/Sulfur Cell," *J. Power Sources.* 9: 281 (1983); Peled et al., "Lithium-Sulfur Battery: Evaluation of Dioxolane-Based Electrolytes," *J. Electrochem. Soc..* 136 (6): 1621 (June 1989); Bennett et al., U.S. Pat. No. 4,469, 761; Farrington and Roth, U.S. Pat. No. 3,953,231; Nole and Moss, U.S. Pat. No. 3,532,543; Lauck, H., U.S. Pat. Nos. 3,915,743 and 3,907,591; Societe des Accumulateurs Fixes et de Traction, "Lithium-sulfur battery," Chem. Abstracts. 66: Abstract No. 111055d at page 10360 (1967); and Lauck, H. "Electric storage battery with negative lithium electrode and positive sulfur electrode," *Chem. Abstracts.* 80: Abstract No. 9855 at pages 466–467 (1974).).

Unfortunately, electrolyte solvents employed in most prior art sulfur cells were not developed for the sulfur electrode. Further, the low molecular weight solvents (e.g., tetrahydrofuran and dimethoxyethane) employed in many of these of systems would be quite hazardous in commercial batteries. This is because they are flammable and have a high vapor pressure. Thus, they are difficult to control during manufacture, and there is always the danger of combustion or explosion in a commercial cell.

What is needed therefore is a safe liquid electrolyte metal-sulfur battery system optimized for the chemical and electrochemical features of the sulfur rechargeable electrode.

SUMMARY OF THE INVENTION

The present invention provides high performance thin film lithium-sulfur battery cells having liquid electrolytes. The cells are preferably rechargeable, having (1) a minimum sulfur utilization of at least about 10% (more preferably at least about 20% and most preferably at least about 30%) over at least 50 cycles (more preferably over at least 100 cycles and even more preferably over at least 200 cycles) or (2) a sulfur utilization of at least 50% over at least 2 cycles (more preferably over at least about 10 cycles and even more preferably over at least about 75 cycles). To attain such high performance, the cells' configuration and electrolyte should be carefully selected. The thin film cells of this invention will be characterized by a relatively small separation distance between electrodes. If a cell's "separation distance" is defined as the distance between a back boundary where the catholyte is farthest removed from the negative electrode and a front boundary where the catholyte is nearest the negative electrode, that separation distance is preferably not more than about 400 (micrometer)($cm^2$)mA/$i_1$. In this expression, $i_l$ is the maximum steady state current density under which the cell operates. Thus, as the cell's maximum current density increases, its separation distance should decrease. If this design criteria is followed, the amount of precipitated discharge product should be minimized. In order that the cell operate at steady state current densities suitable for commercial applications, the cell should be able to discharge at least about 0.5 mA/$cm^2$ over 50 cycles.

In an especially preferred embodiment, the separation distance is not more than about 300/$i_1$ and even more preferably, not more than about 200/$i_1$. In absolute terms, the separation distance preferably will be not more than about 300 micrometers, and more preferably not more than about 150 micrometers.

Preferably, the liquid electrolyte in such thin film metal-sulfur cells has dissolved therein between about 3 and 30 molar atomic sulfur (in the form of sulfides and/or polysulfides). In general, the higher the sulfur concentration, the higher the cell's capacity. However, if the sulfur concentration becomes too great, large amounts of sulfide and/or polysulfide may precipitate out of solution.

The present invention also provides liquid electrolyte solvents for ambient-temperature metal-sulfur batteries (e.g., lithium-sulfur batteries). Preferred solvents include at least one compound having an ethoxy repeating unit. These solvents have the general formula $R_1(CH_2CH_2O)_nR_2$, where n ranges between 2 and 10 and $R_1$ and $R_2$ are different or identical alkyl or alkoxy groups (including substituted alkyl or alkoxy groups). Alternatively, $R_1$ and $R_2$ may together with $(CH_2CH_2O)_n$ form a closed ring. Examples of linear solvents include the glymes $(CH_3O(CH_2CH_2O)_nCH_3)$, and glyme derivatives such as $((CH_2CH_2O)_n(CH_2O)_p)$, where p ranges between about 1 and 50. In an alternative embodiment, the electrolyte solvent includes a cryptand or crown ether as a cosolvent. Certain cryptands and crown ethers strongly coordinate lithium.

The above ethoxy repeating unit compounds typically serve as lithium ion coordinating solvents. Preferred electrolyte solvents include a donor or acceptor cosolvent in addition to an ethoxy compound as described. Preferred donor solvents have a donor number of at least about 15, more preferably between about 15 and 40 and most preferably between about 18–40. Examples of donor solvents include hexamethylphosphoramide, pyridine, N,N-diethylacetamide, N,N-diethylformamide, dimethylsulfoxide, tetramethylurea, N,N-dimethylacetamide, N,N-dimethylformamide, tributylphosphate, trimethylphosphate, N,N,N',N'-tetraethylsulfamide, tetramethylenediamine, tetramethylpropylenediamine, and pentamethyldiethylenetriamine. These assist in solvation of lithium ions. Examples of acceptor solvents include protic and aprotic solvents such as methanol, ethylene glycol, polyethylene glycol, nitromethane, trifluoroacetic acid, trifluoromethanesulfonic acid, sulfur dioxide, and boron trifluoride. These assist in solvation of the sulfide and polysulfide anions.

In general, the main solvents of this invention will have relatively low ambient temperature vapor pressures (at least in comparison to dimethoxyethane). Thus, to ensure that the solvent's molecular weight is sufficiently high to provide a relatively low vapor pressure, "n" must be 2 or greater. In keeping with the general desire that the electrolyte be liquid at ambient temperature, the value of n should generally not exceed 10.

These and other features of the invention will be further described and exemplified in the drawings and detailed description below.

BRIEF DESCRIPTION OF THE DRAWINGS

FIG. 2B is a block diagram of lithium/liquid electrolyte/sulfur cell in accordance with yet another embodiment of this invention.

FIG. 3B is a table presenting various slurry compositions employed to fabricate sulfur electrodes for use in cells of this invention.

FIG. 4 is a table presenting the results of various experiments conducted in accordance with this invention.

DETAILED DESCRIPTION OF THE PREFERRED EMBODIMENTS

Introduction

Figure 1:
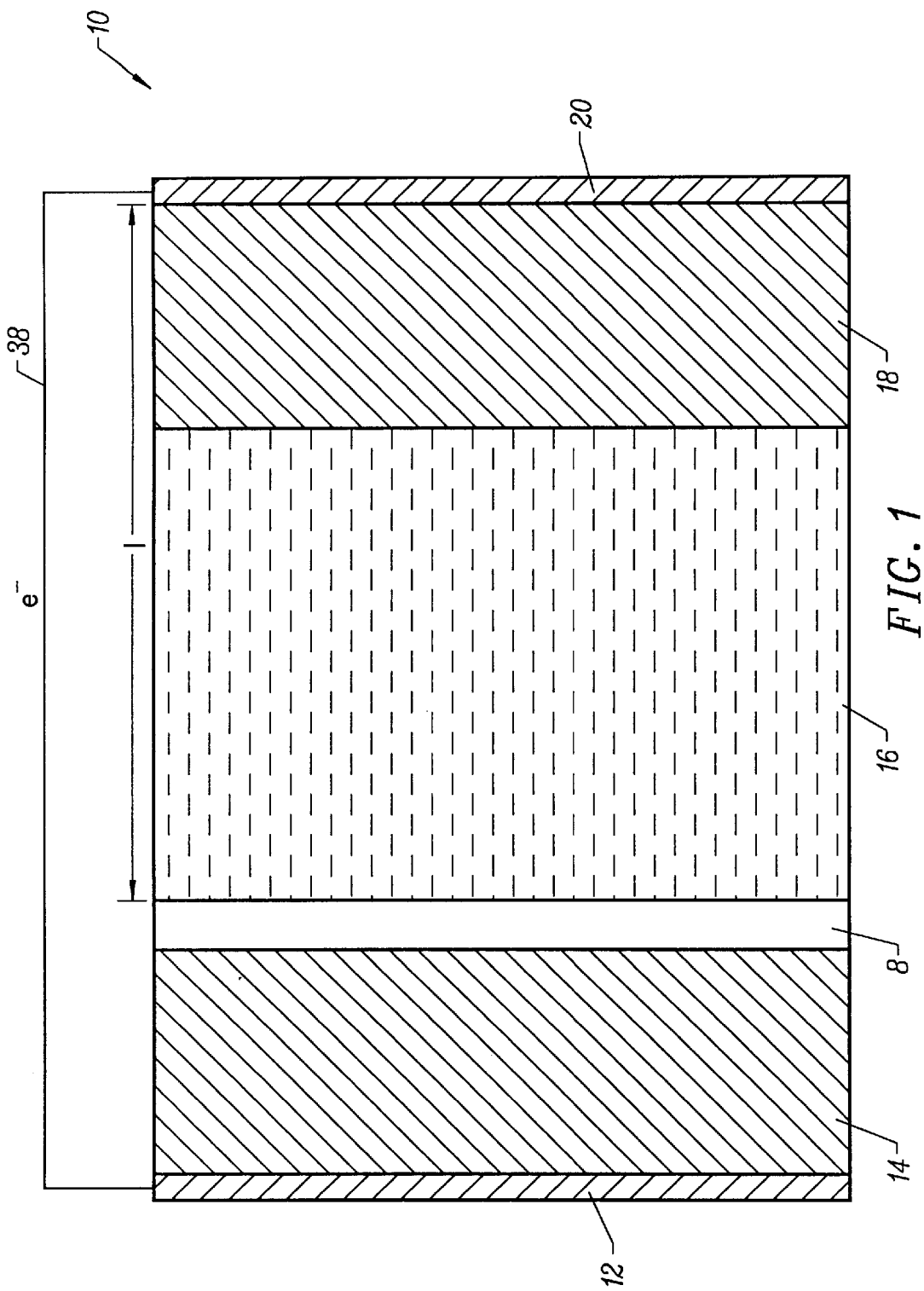
FIG. 1 is a block diagram of a lithium/liquid electrolyte/sulfur cell of this invention.

This invention provides metal-sulfur batteries having low equivalent weight, high cell voltage and consequently a high specific energy, and operating at high sulfur utilization over many cycles. The batteries are preferably constructed in a thin film format such that the current density does not become diffusion limited.

In one embodiment, the battery cells of this invention include a liquid electrolyte solvent that may have repeating ethoxy units ($CH_2CH_2O$). Preferably, the main electrolyte solvent includes a glyme or related compound. Such solvents are believed to strongly coordinate lithium and thereby increase the solubility of discharge products of lithium-sulfur batteries.

The positive electrodes employed in batteries of this invention include a sulfur-based material having a relatively low equivalent weight. The electrodes, which may be composites, include in their theoretically fully charged state sulfur and an electronically conductive material. At some state of discharge, the positive electrode will include one or more of sulfides and polysulfides, which are sulfides and polysulfides of the metal or metals found in the negative electrode. In some embodiments, the fully charged electrode may also include some amount of such sulfides and/or polysulfides.

Sometimes the sulfur-based electroactive material in a positive electrode may be generally referred to as "active sulfur." As used herein, that term refers to electroactive material that is elemental sulfur or discharge products of elemental sulfur that would return to elemental sulfur in a theoretically fully charged state.

Upon discharge, the sulfur of the positive electrode reacts with the metal of the negative electrode to form the metal sulfides and polysulfides. For example, where M is the metal of the negative electrode, the overall cell reaction can be described as follows:

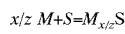

$$x/z\ M+S=M_{x/z}S$$

where M is any metal that can function as an active component in a negative electrode in a battery cell in which sulfur is the active component of the positive electrode; x=0 through x=2; z=the valence of the metal; and S is sulfur.

M is preferably at least one of an alkali metal, an alkaline earth metal, and a transition metals. M is more preferably selected an alkali metal, and still more preferably lithium or sodium. M is most preferably lithium.

In a preferred embodiment of this invention where the negative electrode contains lithium, the overall cell reaction wherein z=1 can be described as follows:

$$xLi+S=Li_xS.$$

When x=2, 100% of the theoretical specific energy of the system has been released. If all elemental sulfur in the positive electrode reacts completely (so that all sulfur resides in $Li_2S$), the sulfur in the electrode is 100% utilized so that all 1675 mAh/g of sulfur is extracted during discharge.

From the above discussion, it should be apparent that upon discharge the positive electrode becomes a combination of sulfur, metal sulfides and polysulfides, and during the discharging process the proportions of those sulfur-containing components will change according to the state of charge. The charge/discharge process in the positive electrode is reversible. Similarly, upon recharging, the percentages of the sulfur-containing ingredient will vary during the process.

The positive electrode is fabricated such that it permits electrons to easily move between the sulfur and the electronically conductive material, and permits ions to move between the electrolyte and the sulfur. Thus, high sulfur utilization is realized after many cycles.

The present invention contemplates cell designs in which (1) all active sulfur is dissolved in electrolyte solution (one phase positive electrode) and (2) cell designs in which the active sulfur is distributed between a solid phase (sometimes precipitated) and a liquid phase. Each design has its advantages. The first design (all sulfur is dissolved in the electrolyte) can be operated without producing precipitated active sulfur. Thus, there is less danger of the cell capacity being reduced due to unavailable precipitated electroactive species. The second design has a greater capacity because the solid phase active sulfur contains a higher density of electroactive material. While the second design does have to contend with precipitated active sulfur and the possibility that electroactive species will be lost, certain design criteria can be employed to mitigate this potential detriment. For example, the cell can be configured or operated under conditions to minimize precipitation. These configurations and conditions are the subject of this invention.

In a two phase design, the range of sulfur in such electrodes in the theoretically fully charged state is preferably from about 10% to 90% (more preferably 30% to 80%) by weight, excluding electrolyte. The sulfur-based composite electrode is preferably processed such that the component particles are homogeneously distributed, and segregation and/or agglomeration of the component particles is avoided.

A metal-sulfur battery system constructed with the sulfur-based positive electrode of this invention should have at least about 10%, and more preferably at least about 30%, availability of the sulfur, and most preferably at least about 50% availability of sulfur (during a single cycle). This availability corresponds to a minimum of 168 mAh/g (more preferably 504 mAh/g and most preferably 838 mAh/g) of sulfur included in the positive electrode. This is based on the above-mentioned theoretical value of 1675 mAh/gm of sulfur at 100% availability.

Battery Design

Suitable batteries may be constructed according to the known art for assembling cell components and cells as desired, and any of the known configurations may be fabricated utilizing the invention. The exact structures will depend primarily upon the intended use of the battery unit. Examples include thin film with porous separator, thin film polymeric laminate, jelly roll (i.e., spirally wound), prismatic, coin cell, etc.

The negative electrode is spaced from the positive sulfur electrode, and both electrodes may be in material contact with an electrolyte separator. Current collectors contact both the positive and negative electrodes in a conventional manner and permit an electrical current to be drawn by an external circuit. In a typical cell, all of the components will be enclosed in an appropriate casing, for example, plastic, with only the current collectors extending beyond the casing. Thereby, reactive elements, such as sodium or lithium in the negative electrode, as well as other cell elements are protected.

Thin film configurations of this invention will be described in more detail below. Other more conventional cell designs are known in the art which may be consulted for details. Examples of sulfur cells employing non-thin film design are set forth in the following references which are incorporated herein by reference for all purposes: (1) R. D. Rauh, F. S. Shuker, J. M. Marston and S. B. Brummer, J. Inorg. Nuc. Chem., "Formation of Lithium Polysulfides in Aprotic Media", 39, 1761 (1977); (2) R. D. Rauh, K. M. Abraham, G. F. Pearson, J. K. Suprenant and S. B. Brummer, "A Lithium/Dissolved Sulfur Battery with an Organic Electrolyte," J. Electrochem. Soc., 126, 523 (1979); (3) H. Yamin, A. Gorenshtein, J. Penciner, Y. Sterberg, and E. Peled, "Lithium Sulfur Battery," J. Electrochem. Soc., 135, 1045 (1988); (4) H. Yamin and E. Peled, "Electrochemistry of a Nonaqueous Lithium/Sulfur Cell," J. Power Sources, 9, 281 (1983); and (5) E. Peled, Y. Sterberg, A. Gorenshtein, and Y. Lavi, "Lithium-Sulfur Battery: Evaluation of Dioxolane-Based Electrolyte," J. Electrochem. Soc., 136, 1621 (1989).

Referring now to FIG. 1, a cell 10 in accordance with a preferred embodiment of the present invention is shown. Cell 10 includes a negative current collector 12 which is formed of an electronically conductive material. The current collector serves to conduct electrons between a cell terminal (not shown) and a negative electrode 14 (such as lithium) to which current collector 12 is affixed. If negative electrode 14 is made from lithium or other similarly reactive material, it will preferably include a protective layer 8 formed opposite current collector 12. Either negative electrode 14 or protective layer 8 (if present) contacts a liquid electrolyte in an electrolyte region 16.

Region 16 may be delineated by the boundaries of a separator which prevents electronic contact between the positive and negative electrodes. A positive electrode 18 abuts the side of separator layer 16 opposite negative electrode 14. As electrolyte region 16 is an electronic insulator and ionic conductor, positive electrode 18 is ionically coupled to but electronically insulated from negative electrode 14. Finally, the side of positive electrode 18 opposite electrolyte region 16 is affixed to a positive current collector 20. Current collector 20 provides an electronic connection between a positive cell terminal (not shown) and positive electrode 18.

Current collectors 12 and 20, which provides current connections to the positive and negative electrodes, should resist degradation in the electrochemical environment of the cell and should remain substantially unchanged during discharge and charge. In one embodiment, the current collectors are sheets of conductive material such as aluminum, copper, or stainless steel. The positive electrode may be attached to the current collector by directly forming on the current collector or by pressing a pre-formed electrode onto the current collector. Positive electrode mixtures formed directly onto current collectors preferably have good adhesion. Positive electrode films can also be cast or pressed onto expanded metal sheets. Alternately, metal leads can be attached to the positive electrode by crimp-sealing, metal spraying, sputtering or other techniques known to those skilled in the art. The sulfur-based positive electrode can be pressed together with the electrolyte separator sandwiched between the electrodes. In order to provide good electrical conductivity between the positive electrode and a metal container, an electronically conductive matrix of, for example, carbon or aluminum powders or fibers or metal mesh may be used.

In the case where sulfur is provided entirely as a dissolved species in the electrolyte, positive electrode 18 may primarily include an electronic conductor such as a carbon fiber matrix together with a binder or other additives. In the case where sulfur is provided in both the solid and liquid (dissolved) phases, positive electrode 18 will include some amount of active sulfur in conjunction with the electronic conductor and possibly additives.

The separator may occupy all or some part of electrolyte compartment 16. Preferably, it will be a highly porous/permeable material such as a felt, paper, or microporous plastic film. It should also resist attack by the electrolyte and other cell components under the potentials experienced within the cell.. Examples of suitable separators include glass, plastic, ceramic, and porous membranes thereof among other separators known to those in the art. In one specific embodiment, the separator is Celgard 2300 or Celgard 2400 available from Hoechst Celanese of Dallas, Texas.

The separator may also be of the type sometimes referred to as a "polymer" separator membrane having a porous or microporous network for entraining liquid electrolyte. Such separators are described in U.S. Pat. No. 3,351,495 assigned to W. R. Grace & Co. and U.S. Pat. Nos. 5,460,904, 5,540,741, and 5,607,485 all assigned to Bellcore, for example. These patents are incorporated herein by reference for all purposes.

In some embodiments of the invention, the cell may be characterized as a "thin film" or "thin layer" cell. Such cells possess relatively thin electrodes and electrolyte separators. Preferably, the positive electrode is no thicker than about 300 $\mu$m, more preferably no thicker than about 150 $\mu$m, and most preferably no thicker than about 100 $\mu$m. The negative electrode preferably is no thicker than about 100 µm and more preferably no thicker than about 100 µm. Finally, the electrolyte separator (when in a fully assembled cell) is no thicker than about 100 µm and more preferably no thicker than about 40 µm.

Various thin film formats are possible. FIG. 1 presents one example. In this example, a "separation distance," 1, defining a critical dimension of thin film batteries of this invention is shown. Generally, the separation distance I defines the boundaries of the region where the cell catholyte resides. More specifically, the separation distance is the distance between a back boundary where the catholyte is farthest removed from the negative electrode and a front boundary where the catholyte is nearest the negative electrode.

Figure 2A:
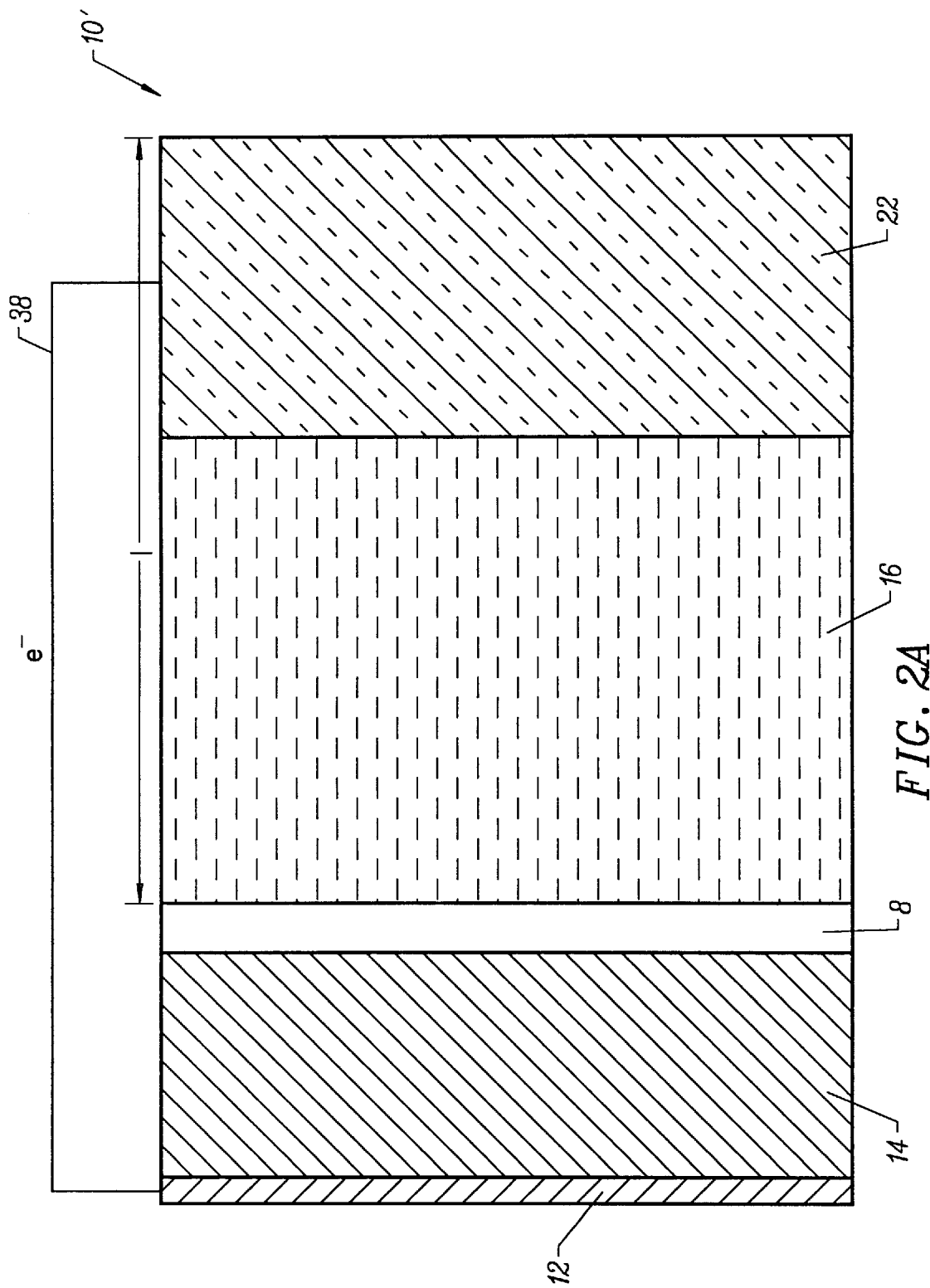
FIG. 2A is a block diagram of lithium/liquid electrolyte/sulfur cell in accordance with another embodiment of this invention.

Other examples of thin film cell formats and their associated separation distances are presented in FIGS. 2A and 2B. FIG. 2A depicts a cell 10' in which a region 22 includes a positive current collector that is co-extensive with the positive electrode. Otherwise, this cell is identical to the one shown in FIG. 1. Note also that the "separation distance" extends from the electrolyte facing side of protective layer 8 (front boundary) all the way to the backside of current collector/positive electrode region 22 (back boundary). In this embodiment, the current collector is preferably a conductive foam or the conductive expanded matrix such as an expanded metal or other thin conductive grid such as metal-coated polymer fibers or weaves. The positive electrode material is interspersed throughout the matrix provided by the current collector.

FIG. 2B shows a related "symmetrical" version 10" of the cell shown in FIG. 2A. Again, the positive electrode is provided coextensively with a foam or expanded current collector in region 22. In this case, however, region 22 is straddled by two separated electrolyte regions 16 each of which abuts a negative electrode 14 with protective layer 8. In this case, the back boundary of separation distance, 1, is provided at the center of region 22.

Electrochemical and Chemical Mechanisms of Lithium-Sulfur Liquid Electrolyte Batteries Referring again to FIG. 1, lithium-sulfur cell 10 will be described with relevant reaction mechanisms explained. During normal charging, the electrons are extracted from positive electrode 18 and transported over electrical connection 38 to negative electrode 14. The removal of electrons at positive electrode 18 oxidizes the species present in the electrode. In this reaction, lithium ions are liberated from lithium sulfide and/or lithium polysulfide species present in the positive electrode. The species remaining in the positive electrode will have the general formula $Li_2S_x$, where x has a value of 1 or greater. Over time the charge reaction produces polysulfide species having longer and longer sulfur chains. It is known for example that in a normal charge reaction, the value of x in some polysulfides may be 12 or greater. In addition, some of the polysulfides will be further oxidized to elemental sulfur.

At the negative electrode, lithium ions present in the electrolyte 16 are transported through protective layer 8 and reduced to lithium metal as electrons are moved through electrical conduit 38.

The above electrode reactions proceed in the reverse direction during discharge. That is, the electrochemical reduction of active sulfur pulls electrons to positive electrode 18 through current collector 20 and from line 38. This reduces elemental sulfur, if present, to form various lithium species including lithium polysulfides and lithium sulfide. It also reduces the highly oxidized polysulfides to less oxidized polysulfides and lithium sulfide. Simultaneously, lithium ions are provided from negative electrode 14 through the electrolyte. The lithium ions are generated in conjunction with the flow of electrons from negative electrode 14 to line 38 (via current collector 12).

Generally, the higher molecular weight polysulfides (those with more sulfur atoms) are more highly soluble than their lower molecular weight counterparts. During discharge, these higher molecular weight species go into solution in the electrolyte and migrate throughout the cell. Some of the dissolved species move to the negative lithium metal electrode where they may be chemically reduced to form less-soluble lower molecular weight compounds such as lithium sulfide. Some of this lithium sulfide may beneficially act as a protective layer on the lithium metal electrode. However, lithium sulfide formed in excess of this beneficial amount may precipitate out a solution where it serves no beneficial use in the cell. In fact, this precipitated lithium sulfide (and/or less-soluble lower molecular weight polysulfides) represents lithium and sulfur that is no longer available for immediate participation in electrochemical reactions. Thus, precipitation of these compounds reduces the battery's capacity.

Precipitated sulfide or polysulfide may also form because the local solution concentration of these species exceeds their solubility limits. This occurs when the species are generated faster than they can diffuse away, a condition that exists when the local current density is too great in comparison with the mass transport rate. That is, the solution phase concentration gradient must support a mass flux that is sufficiently high to remove reaction products before they accumulate to their solubility limit. The present invention addresses this problem in at least two ways. First, it provides electrolyte solvents in which the discharge species are highly soluble and highly mobile thereby reducing the likelihood of precipitation. Second, it provides a thin film cell design in which the mass flux is sufficiently fast that the local concentration of soluble species does not exceed the solubility limits.

Assuming that some precipitation will occur so that solid phase sulfur, sulfide, and/or polysulfide exist in the cell, it is important that the cell be designed to make these precipitated electroactive species available to electronic and ionic charge carriers. This allows high utilization of the active sulfur in the cell. To this end, the electronic conductor in the positive electrode should form an interconnected matrix so that there is always a clear current path from the positive current collector to any position in the electronic conductor. The interconnected matrix of the electronic conductor should also be sufficiently "open" that there is room for precipitated electroactive species to deposit on the matrix. Finally, any binder employed in the positive electrode should not prevent contact between the electronic conductor and the electroactive species. For example, the binder should not provide so much wetting that precipitated sulfur particles and/or the current collector are completely wetted and therefore unable to exchange electrons.

Thin Film Cell Design

As noted, it will be desirable to provide the cells of this invention in a thin film format. This has several advantages. First, such cells may be stacked together to form a battery. In this configuration, the battery electrodes possess a relatively high surface area per unit mass of electrode. Thus, the local current density in the battery is kept relatively low, thereby holding the cell reactions relatively close to equilibrium. This has the benefit of maintaining a relatively uniform current density over the electrode surfaces. Cells with highly non-uniform current densities typically have short life spans because the regions of high current density consume (and generate) greater quantities of cell reactants. As a consequence, reaction products (e.g., plated lithium and lithium sulfide) build up faster at regions of high current density. This can create undesirable mossy lithium deposits and precipitation of sulfides and polysulfides. The uneven distribution of electrode materials (including precipitates) grows with continued cycling until the cell is destroyed.

As a further advantage, the thin film configuration provides a steep concentration gradient for a small concentration difference because of the relatively small separation between the electrodes. This then supports a greater mass flux of discharge products and allows the cell to operate at higher current densities.

Insufficient mass flux in the vicinity of the positive electrode will cause the local sulfide and/or polysulfide concentration to build to a level exceeding the solubility limit, at which point detrimental precipitation occurs.

To design a thin film cell with an appropriately thin separation distance, the following analysis may be employed. It may be assumed that the dominant limiting mode of mass transfer within the liquid electrolyte is diffusion. Steady state diffusion is governed by Fick's first law which may be written for electrochemical systems as follows:

$$i_1 = (D \Delta C F)/l$$

In this expression, $i_1$ is the diffusion limited current density of the system, $1$ is the separation distance within the catholyte region (as exemplified above with respect to FIGS. 1, 2A, and 2B), D is the diffusion coefficient for the current carrying species, $\Delta C$ is the change in concentration across the catholyte region separation distance, and F is the Faraday constant, $9.6845 \times 10^4$ coulombs per mole.

If both the concentration difference, $\Delta C$, across the catholyte region and the average diffusivity, D, of the discharge species can be approximated, then the cell's separation distance can be approximated for the maximum current density, $i_1$, expected during normal operation. A cell then fabricated with a separation distance no greater than that value calculated from the above Fick's law analysis should perform better than a cell having a larger separation distance.

Assuming that the product of F, D, and $\Delta C$ is approximately 100 mA/(cm$^2$ micrometer), then the separation distance for various current densities is provide in the Table below.

TABLE

| MAXIMUM CURRENT (mA) | SEPARATION DISTANCE (Microns) |
|---|---|
| 10 | 10 |
| 9 | 11 |
| 8 | 13 |
| 7 | 14 |
| 6 | 17 |
| 5 | 20 |
| 4 | 25 |
| 3 | 33 |
| 2 | 50 |
| 1 | 100 |
| 0.8 | 125 |
| 0.6 | 167 |
| 0.4 | 250 |
| 0.2 | 500 |
| 0.15 | 667 |
| 0.1 | 1000 |
| 0.05 | 2000 |

Some thin film cell designs within the scope of this invention provide a separation distance, 1, which is defined by $$1 = (D \Delta C F)/i_1$$

where $i_1$ is the maximum current density at which the cell is operated. Generally, it will be expected that the cell will operate at a maximum steady state current density of 0.1 mA/cm$^2$ over at least about 50 cycles. More preferably, the separation distance will be designed to account for a maximum steady state current density of at least about 0.5 mA/cm$^2$ over at least about 100 cycles.

For many systems, the following design criteria may be employed:

$$1 = A/i_1$$

where A is preferably 400 microns/(mA/cm2), more preferably 300 microns/(mA/cm$^2$), and most preferably 200 microns/(mA/cm$^2$).

Liquid Electrolytes

It has now been discovered that the performance of lithium-sulfur batteries can be improved by employing electrolyte compositions designed to solubilize lithium sulfide and relatively low molecular weight polysulfides. The new electrolytes of this invention are in fact designed to keep more sulfur discharge products in solution and therefore available for electrochemical reaction. In general, the electrolyte compositions of this invention include one or more solvents that strongly coordinate lithium. These solvents are "ionophores" for lithium ions. Exemplary ionophores are podands, coronands, and cryptands as described in chapter 10 of the treatise "Lithium Chemistry, A Theoretical and Experimental Overview," Anne-Marie Sapse and Paul Von Rague Schleyer, Eds. John Wiley & Sons, New York (1995) which is incorporated herein by reference for all purposes. Chapter 10 was written by Bartsch et al. Podands are acyclic multidentate ligands. Common examples are glymes and polyethylene glycols. Coronands are monocyclic multidentate ligands. Common examples are crown ethers and substituted crown ethers. Cryptands are multicyclic multidentate ligands.

In a preferred embodiment, the electrolyte solvents of this invention include one or more compounds having an ethanediether linkage. They have the general formula $R_1(CH_2CH_2O)_nR_2$, where n ranges between 2 and 10 and $R_1$ and $R_2$ are different or identical alkyl or alkoxy groups (including substituted alkyl or alkoxy groups). Alternatively, $R_1$ and $R_2$ may together form a closed ring to form a crown ether for example. Examples of linear solvents include the glymes ($CH_3O(CH_2CH_2O)_nCH_3$) and related oxides of the formula $(CH_2CH_2O)_n(CH_2O)_p$, where p ranges from about 1 to 50. Such ethoxy repeating unit compounds serve as lithium ion coordinating solvents. In a preferred embodiment, the main solvent is a glyme having a value of n ranging between 3 and 6. In an especially preferred embodiment, the glyme is tetraglyme ($CH_3O(CH_2CH_2O)_4CH_3$).

The batteries of this invention can operate at room temperature. However, the present invention also pertains to systems operating at temperatures slightly outside of the ambient. Obviously, the choice of operating temperature ranges can influence the preferred electrolyte for the batteries of this invention. For example, at relatively low operating temperatures, lower molecular weight electrolytes will be preferred, so the value of "n" in the above-describe ethanediether compounds will be in the lower end of the 2–10 range. At higher temperatures, the opposite is true.

While the electrolyte solvents described above are a main component of the electrolytes of this invention, one or more cosolvents may be provided with them. If such cosolvents are employed, they are preferably chosen to solubilize lithium cations or sulfide/polysulfide anions. In certain preferred embodiments, crown ethers and/or cryptands are provided as cosolvents. In other preferred embodiments, donor or acceptor cosolvents may be employed.

Crown ethers are macrocyclic polyethers generally having repeating ethoxy and/or propoxy groups. Crown ethers with 3 to 20 oxygen atoms have been synthesized. They are typically made up of linked ethoxy units $(CH_2CH_2O)_n$ as shown below. A general abbreviation used is n-C-m where n is the ring size and m is the number of oxygen atoms in the ring. For example the structure shown below is 12-crown-4.

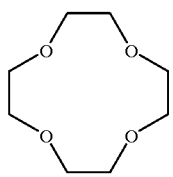

Commercially available crowns which have application in this invention include 12-crown-4, 15-crown-5, 18-crown-6, and modified crowns such as dibenzo-18-crown-6. Crown ethers are known to be complexing agents which solubilize alkali metal cations in nonpolar solvents. 12-crown-4 is known to be specific for the lithium cation.

In substituted crown ethers, one or more of the hydrogen atoms are replaced with a hydrocarbon group that may be linear, branched, or aromatic. These hydrocarbon groups may, in turn, be substituted with halo (F, Cl, Br, I), nitrile (CN), nitro ($NO_2$), hydroxy (OH), and other common substituent groups. Examples are presented in chapter 10 of the above referenced "Lithium Chemistry" treatise. Specific examples include dibenzo-14-crown-4, tetramethyl-12-crown4, benzo-15-crown-5. Crown ethers may also be substituted with podand groups such as ($-COCH_2CH_2OCH_3$) to form podano-coronands or "lariat ethers."

In an alternative embodiment, the main solvent is a cryptand. Cryptands are also known to strongly complex with alkali metal cations. Structurally, they are similar to crown ethers but possess an additional ($-XCH_2CH_2$) bridge to create an additional ring. X may be an oxygen, nitrogen, or sulfur atom. Often X is nitrogen and the corresponding cryptands are described as containing two nitrogen atoms linked by three $(CH_2CH_2O)_n$ bridges. These compounds are commonly identified by the number of oxygen atoms in each of the three bridges. Thus, a cryptand in which two of the bridges have n=2 (two oxygen atoms) and a third bridge having n=1 (one oxygen atom) is identified as [2.2.1]-cryptand.

Examples of other general classes of cosolvents are donor solvents which tend to solubilize cations and acceptor solvents which tend to solubilize anions. Donor solvents are characterized by high donor numbers DN. A desirable property of both donor and acceptor cosolvents used in this invention is a high dielectric constants, $\epsilon$. Such solvents generally promote dissociation of an ionic solute or a contact ion-pair.

Generally, donor solvents are those solvents which can be characterize as Lewis bases (they may be aprotic solvents). Generally, these solvents are good at solvating cations such as lithium ions. Donor solvents promote the ionization of covalent compounds to form intimate (or contact) ion-pairs. The concept of a solvent donor number is further explained and exemplified in "Experimental Electrochemistry for Chemists," by Sawyer and Roberts, Jr., John Wiley & Sons, New York (1995). That reference is incorporated herein by reference for all purposes.

Suitable donor cosolvents include hexamethylphosphoramide, pyridine, N,N-diethylacetamide, N,N-diethylformamide, dimethylsulfoxide, tetramethylurea, N,N-dimethylacetamide, N,N-dimethylformamide, tributylphosphate, trimethylphosphate, N,N,N',N'-tetraethylsulfamide, tetramethylenediamine, tetramethylpropylenediamine, and pentamethyldiethylenetriamine. These assist in solvation of lithium ions.

Suitable acceptor solvents assist in solvation of the sulfide and polysulfide anions. Acceptor solvents are those solvents which can be characterized as Lewis acids (they may be protic or aprotic solvents) and promote solvation of anions. Examples include alcohols such as methanol, glycols such as ethylene glycol, and polyglycols such as polyethylene glycol, as well as nitromethane, trifluoroacetic acid, trifluoromethanesulfonic acid, sulfur dioxide, and boron trifluoride.

It should be understood that the electrolyte solvents of this invention may also include other cosolvents which do not necessary fall into the donor solvent and acceptor solvent classes. Examples of such additional cosolvents include sulfolane, dimethyl sulfone, dialkyl carbonates, tetrahydrofuran (THF), dioxolane, propylene carbonate (PC), ethylene carbonate (EC), dimethyl carbonate (DMC), butyrolactone, N-methylpyrrolidinone, dimethoxyethane (DME or glyme), and combinations of such liquids.

In general, the liquid electrolyte solvents of this invention include about 50 to 100% by weight of the main solvent (excluding salts) which is usually one or more podand such as the above-described ethanediether compounds. The balance will be one or more of the cosolvents listed above. More preferably, the electrolyte solvents include about 50 to 100% by weight main solvent, and most preferably between about 70 and 90% by weight main solvent. As noted, the main solvent is one or more of the lithium coordinating ionophores described above (podands such as glymes, coronands such as crown ethers, or cryptands). Aside from the main solvent, the electrolyte solvent may include one or more cosolvents (described above) which make up the balance.

Exemplary but optional electrolyte salts for the battery cells incorporating the electrolyte solvents of this invention include, for example, lithium trifluoromethanesulfonimide ($LiN(CF_3SO_2)_2$), lithium triflate ($LiCF_3SO_3$), lithium perchlorate ($LiClO_4$), $LiPF_6$, $LiBF_4$, $LiAsF_6$, as well as, corresponding salts depending on the choice of metal for the negative electrode, for example, the corresponding sodium salts. As indicated above, the electrolyte salt is optional for the battery cells of this invention, in that upon discharge of the battery, the metal sulfides or polysulfides formed can act as electrolyte salts, for example, $M_{x/z}S$ wherein x=0 to 2 and z is the valence of the metal.

Regardless of whether the sulfur is present in a solid phase, the cells of this invention preferably operate with their electrolytes at a concentration of between about 3 and 30 molar sulfur, more preferably between about 7 and 25 molar sulfur, and most preferably between about 10 and 20 molar sulfur. The sulfur used in this measure is the sulfur atoms in electroactive species. Thus, for example, one molar $Li_2S$ corresponds to one molar sulfur, whereas one molar $Li_2S_5$ corresponds to five molar sulfur, and one molar $S_8$ corresponds to eight molar sulfur.

It should be understood that some systems employing liquid electrolytes are commonly referred to as having "polymer" separator membranes. Such systems are considered liquid electrolyte systems within the context of this invention. The membrane separators employed in these systems actually serve to hold liquid electrolyte in small pores by capillary action. Essentially, a porous or microporous network provides a region for entraining liquid electrolyte. As mentioned above, such separators are described in U.S. Pat. No. 3,351,495 assigned to W. R. Grace & Co. and U.S. Pat. Nos. 5,460,904, 5,540,741, and 5,607,485 all assigned to Bellcore, for example.

Positive Electrode

The positive electrode must utilize an electrochemically active material capable of being reduced during discharge by reaction with metal ions from the negative electrode. In this invention, the electrochemically active material includes some substantial fraction of "sulfur." This does not mean that the positive electrode must rely exclusively upon sulfur for its electrochemical energy, but often this will be the case.

As mentioned, the electroactive sulfur in the positive electrode may be referred to as "active sulfur" which represents sulfur that is elemental or would be elemental in a theoretically fully charged state of the battery. The sulfur of the positive electrode may be defined another way: at least one of elemental sulfur, a sulfide of the metal from the negative electrodes, and a polysulfide of the metal from the negative electrode. These definitions capture positive electrodes in various states of charge. For example, even if the fully charged cell includes only elemental sulfur, a slightly discharged cell will have some of its elemental sulfur reduced to a metal polysulfide or metal sulfide. Further, the theoretically fully charged state of some cells of this invention need not require that the positive electrode be entirely converted to elemental sulfur. It may be possible in some cases to have the positive electrode be a highly oxidized form of lithium polysulfide, for example, as in $Li_2S_x$ where x is five or greater. The fully charged positive electrode may also include a mixture of such polysulfides together with elemental sulfur and possibly even some sulfide. It should be understood that during charge, the positive electrode would generally not be of uniform composition. That is, there will be some amount of sulfide, sulfur, and an assortment of polysulfides with various values of x.

Some or all of the active sulfur components may be dissolved in the electrolyte solvent. If the active sulfur is totally dissolved, then the solid phase structure of the positive electrode simply contains an electronic conductor and possibly some binder or other additive. The sulfur is provided by the solution for reaction at the positive electrode electronic conductor.

Solid phase sulfur positive electrodes of this invention preferably include an electronic conductor in intimate contact with the electrochemically active sulfur. The electrochemically active material must also be in intimate contact with an ion conductor. In the above referenced Chu patents, the ionic conductor typically was a separately added gel or solid state material present in the positive electrode. In the liquid electrolyte batteries of the present invention, the ionic conductor is preferably the electrolyte itself which permeates through the positive electrode and thereby remains in intimate contact with the sulfur (elemental sulfur, metal polysulfides, and/or metal sulfides).

Exemplary electronically conductive materials of the composite positive electrode include carbon black, graphite, carbon fibers, electronically conductive compounds with conjugated carbon-carbon and/or carbon-nitrogen double bonds, for example but not limited to, electronically conductive polymers, such as, polyaniline, polythiophene, polyacetylene, polypyrrole, and combinations of such electronically conductive materials. The electronically conductive materials of the positive electrode may also have electrocatalytic activity.

As mentioned above, the electronic conductor in the positive electrode preferably forms an interconnected matrix so that there is always a clear current path from the positive current collector to any position in the electronic conductor. This provides high availability of electroactive sites and maintained accessibility to charge carriers over repeated cycling. Often such electronic conductors will be fibrous materials such as a felt or paper. Examples of suitable materials include a carbon paper from Lydall Technical Papers Corporation of Rochester, N.H. and a graphite felt available from Electrosynthesis Company of Lancaster, N.Y.

The sulfur is preferably uniformly dispersed in a composite matrix containing an electronically conductive material. Preferred weight ratios of sulfur to electronic conductor in the sulfur-based positive electrodes of this invention in a fully charged state are at most about 50:1, more preferably at most about 10:1, and most preferably at most about 5:1. The sulfur considered in these ratios includes both precipitated or solid phase sulfur as well as sulfur dissolved in the electrolyte. Preferably, the per weight ratio of electronic conductor to binder is at least about 1:1 and more preferably at least about 2:1.

The composite sulfur-based positive electrode may further optionally include performance enhancing additives such as binders, electrocatalysts (e.g., phthalocyanines, metallocenes, brilliant yellow (Reg. No. 3051-114 from Aldrich Catalog Handbook of Fine Chemicals; Aldrich Chemical Company, Inc., 1001 West Saint Paul Avenue, Milwaukee, Wis.) among other electrocatalysts), surfactants, dispersants (for example, to improve the homogeneity of the electrode's ingredients), and protective layer forming additives to protect a lithium negative electrode (e.g., organo-sulfur compounds, phosphates, iodides, iodine, metal sulfides, nitrides, and fluorides). Preferred binders (1) do not swell in the liquid electrolyte and (2) allow partial but not complete wetting of the sulfur by the liquid electrolyte. Examples of suitable binders include Kynar available from Elf Atochem of Philadelphia, Pa., polytetrafluoroethylene dispersions, and polyethylene oxide (of about 900 k molecular weight for example). Other additives include electroactive organodisulfide compounds employing a disulfide bond in the compound's backbone. Electrochemical energy is generated by reversibly breaking the disulfide bonds in the compound's backbone. During charge, the disulfide bonds are reformed. Examples of organodisulfide compounds suitable for use with this invention are presented in U.S. Pat. Nos. 4,833,048 and 4,917,974 issued to DeJonghe et al. and U.S. Pat. No. 5,162,175 issued to Visco et al.

Methods of Making a Positive Electrode:

As mentioned, an important feature of this invention is the ability to provide electrodes having electroactive material (usually sulfur) in intimate contact with an electronic conductor. This facilitates electron transport to and from the active material to allow nearly complete utilization of the active material. Note that good utilization also requires that ions be readily available to the sulfur. This criterion is met by ensuring that, during operation, the sulfur in the positive electrode is in intimate contact with the liquid electrolyte (which provides a necessary ionically conductive medium). Thus, the positive electrode should be made sufficiently permeable to the liquid electrolyte that most all the sulfur contacts electrolyte.

Some relevant details of processes for fabricating positive electrodes suitable for use with this invention are provided in U.S. Pat. No. 5,582,623 (previously incorporated herein by reference). Much discussion in that application focused on three-part positive electrodes which include a gel or solid-state ionic conductor in addition to the sulfur and electronic conductor. The positive electrodes used with the present invention rely on the electrolyte itself as the ionic conductor, and therefore do not require a separate ionic conductor. Nevertheless, the fabrication details provided in the '623 patent are generally applicable to the electrodes employed in the present invention.

Figure 3A:
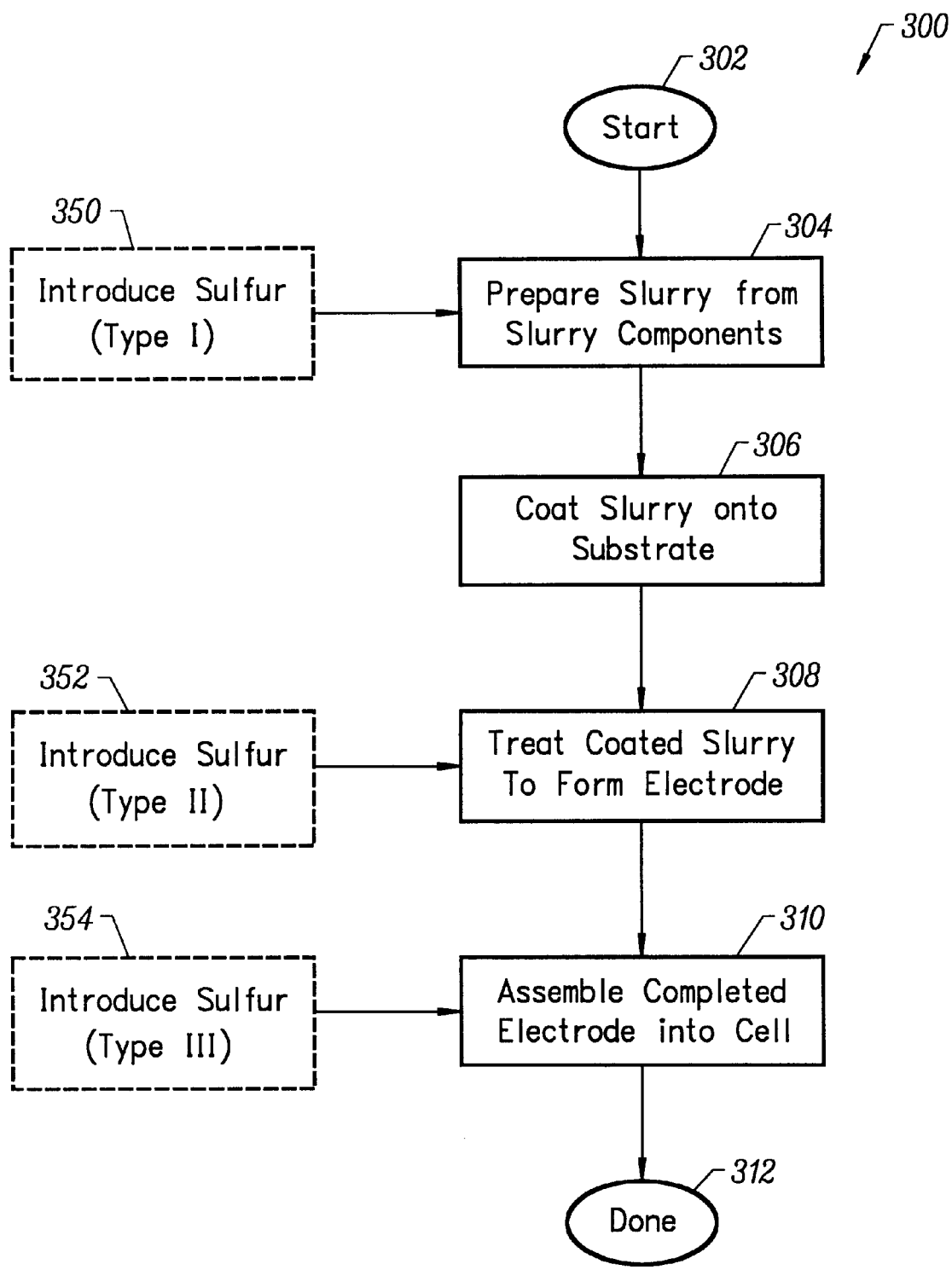
FIG. 3A is a process flow diagram of a preferred method for fabricating positive electrodes that may be employed in this invention.

One process for making positive sulfur-based electrodes suitable for use with this invention is outlined in the flow chart of FIG. 3A. A process 300 begins at 302 and then in a step 304, a slurry is prepared from a liquid and at least some of the positive electrode components. The solid components of the slurry may include active sulfur, an electronic conductor, a dispersing agent, and a binder. After the slurry is formed, it is coated onto a substrate such as a current collector or carbon paper electronic conductor matrix. See step 306. At this point, the slurry liquid may be removed by any number of processes including evaporation. The resulting "preformed positive electrode" may then be treated at a step 308 according to a post coating process such as heating to bind the various solid phase electrode components. At the conclusion of step 308, a completed electrode has been produced. Then, at a step 310, the completed electrode is assembled into a battery cell, with the process being complete at 312.

During process 300, sulfur may be introduced into the positive electrode at various points as indicated by optional steps 350, 352, and 354. The sulfur may be introduced in at least one of these steps. At step 350, sulfur is optionally introduced as one of the solid components to the slurry prepared at step 304. Introduction of sulfur at step 350 is referred to as a "Type I" process. At step 352, sulfur may be introduced during electrode treatment step 308. This is referred to herein as a "Type II" process and typically involves providing a concentrated solution of elemental sulfur to the preformed electrode. Finally, at step 354, sulfur may be introduced to the electrode during cell assembly (step 310) in a "Type III" process. In this case, the sulfur is provided in a concentrated electrolyte solution. It is important to recognize that the sulfur may be added to the electrode at any or more of steps 350, 352, and 354.

In slurry preparation step 304, the procedure should produce a uniform slurry, in which the solids are dispersed, stabilized and de-agglomerized. Details of a particular slurry preparation depends on the type and weight percents of the solids content as well as the type and amount of liquid solvent employed. There are, however, some general procedures that are typical for many of the slurry preparations.

A slurry typically includes solids dispersed and/or dissolved in a liquid phase. Solid slurry components may include an electronically conductive material, a binding agent, a dispersing agent, a solid state and/or gel state ionic conductor, and active sulfur. Typically the solids content in the slurry is uniformly dispersed throughout the liquid phases, but some, all, or none of the solids may be dissolved in the liquid phases.

In a first method of slurry preparation, the active sulfur (if any), the electronically conductive material, and a dispersing agent are stir-mixed in an appropriate solvent until a uniform dispersion is formed. In a preferred embodiment, a dispersing agent is not added to the slurry as it provides no function in the final product and merely adds weight. The ratio of milliliters of solvent to grams of solid material depends on the desired composition and texture of the slurry. Some ranges for the liquids and solids weight percents are presented in the Table shown in FIG. 3B. Once the dispersion is uniformly mixed, the binding agent is gradually added to the dispersion in a step wise fashion while the dispersion is continuously stir-mixed. The gradual addition of the binding agent combined with continuous stir mixing of the dispersion helps to prevent flocculation and the creation of grossly large aggregates. Ranges for the grams of binding agent to milliliters of solvent is also presented in the Table of FIG. 3B. The slurry is made uniform by stir mixing for a period of at least 24 hours followed by placing the slurry through a three roll mill.

In a second method of slurry preparation, the active sulfur, the electronically conductive material and the dispersing agent are stir mixed in an appropriate solvent until the dispersion is uniform. This dispersion is known as dispersion #1. In a preferred embodiment, the dispersing agent is not added to the slurry. The binding agent is added to an appropriate solvent in order to make a second dispersion, known as dispersion #2. Dispersion #2 is also stir mixed until it becomes uniform. Dispersion #2 is then slowly added to dispersion #1 while Dispersion #1 undergoes continuous stir-mixing. The slurry is stir mixed for 24 hours and then put through a three roll mill to make it more uniform.

Representative electronically conductive materials used in the slurry include carbon blacks, graphites, carbon fibers, electronically conductive compounds with conjugated carbon-carbon and/or carbon-nitrogen double bonds, for example but not limited to electronically conductive polymers, such as polyaniline, polythiophene, polyacetylene, polypyrrole, and combinations of such electronically conductive materials. The electronically conductive material in the slurry provides a mechanism for electron transfer and for electronic conduction throughout the positive electrode. The weight percent of electronically conductive material in the solids content of the slurry typically ranges from 15%–85%, but can be as high a 100%.

Representative binding materials that in part comprise the slurry include but are not limited to polymeric materials, such as polyethylene oxide, polyvinylidene fluoride, polyethylene, polytetrafluoroethylene, electronically conductive polymers, such as polyaniline, polythiophene, polyacetylene, polypyrrole, and combinations of such polymeric materials. The binder may be added to the slurry to enhance dispersion of the solids in the slurry and/or to stabilize the solids in the slurry from segregation, aggregation and/or flocculation. The binder may also be added to enhance the mechanical integrity of the positive electrode, to improve mechanical and electrical contact at the solid-solid interface and/or the solid/liquid interface, to increase electronic and/or ionic conduction throughout the composite positive electrode, and still further, to enhance the electrochemical redox reactions. The solids content weight percent of binding materials in the slurry typically ranges from 5%–50%, but can be as low as zero percent.

Representative dispersing agents that in part comprise the slurry include but are not limited to low molecular weight polyethylene glycols, soya lecithin, etc., and such dispersing agents that are well recognized in the field. The solids content weight percent of dispersing agent in the slurry can be as high as 25% and as low as zero percent, but is typically 2%–10%.

Active sulfur may also be added to the slurry, and this type of sulfur loading is known as type I sulfur loading. The active sulfur added to the slurry includes but is not limited to elemental sulfur, sulfides, polysulfides, redox sulfur polymers, and a combination of such sulfur-containing materials.

Liquid phases are typically added to the slurry and can act as vehicles to better disperse, de-agglomerate and or dissolve the solids content. Typical liquid phases include but are not limited to acetonitrile, iso-propyl alcohol, tetrahydrofuran, carbon disulfide, tetraglyme, dibutyl phthalate and acetone.

Cathodes may be coated from the slurry (at step 306) using several variations of a Mayer rod method. In order to make uniform, crack free coatings that remain adhered to the current collector, special attention must be given to the coating process, especially when trying to formulate thicker cathode coatings on a flat sheet current collector. The following methods have been found acceptable.

Method #1

This method is used for thin film coatings on a metallic current collector foil such as Al or stainless steel. A slurry is Mayer rod coated directly onto a metal current collector and the solvent is allowed to evaporate off. The thickness of the coating is controlled by the type of Mayer rod employed, the consistency of the slurry, and the number of Mayer rod passes. For example, a coating thickness of 25 micrometers may be formed with a single pass of a Mayer rod having a wire diameter of 0.078 inches.

Method #2

This method is used for thicker film coatings on a metallic current collector foil such as Al or stainless steel. Method #2 is similar to that described in Method #1, with the main difference being that the coatings are made with Mayer rods that have a pre-defined gap between the Mayer rod and the substrate. In a preferred embodiment, this gap ranges between about 0 and 200 micrometers.

Method #3

This method is used for impregnating slurry in to carbon paper network s and carbon felt materials. In this method the slurry is vacuum impregnated into a carbon paper. The carbon paper is placed on top of a silk screen that is molded to a vacuum plate. Slurry is impregnated into the carbon paper by Mayer rod coating while applying a vacuum to the backside of the carbon paper. The vacuum helps to load the slurry into the paper and allows for a more uniform distribution of slurry through the thickness of the paper. The amount of slurry inserted into the carbon paper depends on the mesh size of the silk screen, the Mayer rod #, the viscosity of the slurry, and, of course, on the number of Mayer rod passes.

As mentioned, in Type II processes, active sulfur is introduced to the electrode during treatment step 308. After the slurry has been coated and dried, either on a flat metal sheet current collector or into a carbon paper network, it is considered a preformed cathode. Preformed cathodes can be treated to a variety of different procedures such as heat treatments, chemical treatments, etc. Possible chemical treatments serve to load additives and/or active sulfur to the cathode. One method for adding active sulfur to the cathode is to dissolve elemental sulfur in an appropriate highly volatile solvent and then to re-crystallize the sulfur on the surface of the preformed cathode.

There are certain advantages of loading sulfur into a preformed cathode in this manner. For example, the electronically conductive network can be formed and optimized such that during sulfur dissolution the electronically conductive network does not break apart under the associated stresses.

The final cell assembly (step 310) may be performed in various manners. One part of the final cell assembly is to insert electrolyte into the cathode structure. If the electrolyte contains dissolved active sulfur, the sulfur loaded during this step is considered to be Type III sulfur loading. Care must be taken that the electrolyte remains within the confines of the cathode. Too much liquid in the battery cell can lead to a detrimental loss of active sulfur away from the carbon electrode. On the other hand, enough electrolyte must be added to the cathode to allow for a continuous pathway for the dissolved sulfur species to move away and then back to the redox sites in the cathode. Moreover, care must be taken to make sure that there is an adequate ionic pathway through the cathode, through the separator, and to the surface of the anode. The method used to insert the electrolyte into the cathode will depend strongly on the pore structure of the cathode and on the volatility of the liquid electrolyte. In general, the less volatile is the electrolyte, the more readily the electrolyte can be loaded into the cathode. On the other hand, volatile solvents typically have lower viscosity and as such may penetrate the cathode pore structure more effectively. The catholyte may be vacuum impregnated into the positive electrode as follows. First, place the catholyte on the electrode. Then, pull a vacuum under the electrode for several minutes. Finally, remove the vacuum.

While the above described process has been described in terms of batchwise steps, it will be apparent to those of skill in the art that many steps of the process may also be performed in a continuous fashion as described in the above-referenced U.S. Pat. No. 5,582,623.

Negative electrode

Most generally, the negative electrode can comprise any metal, any mixture of metals, glass, carbon or metal/carbon material capable of functioning as a negative electrode in combination with the sulfur-based composite positive electrode of this invention. Accordingly, negative electrodes comprising any of the alkali or alkaline earth metals or transition metals (the polyether electrolytes are known to transport divalent ions such as $Zn^{++}$), for example, in combination with the positive electrodes and electrolytes of this invention are within the ambit of the invention, and particularly alloys containing lithium and/or sodium.

Stated another way, the negative electrodes employed in the batteries of this invention may include a metal (in elemental or alloy form) or an ion of that metal as used in, for example, a carbon intercalation electrode or a glass matrix electrode. As explained above, metal ions from this negative electrode combine with elemental sulfur or polysulfides to produce a sulfide and polysulfides of the metal during discharge of the battery. Some of the resulting metal sulfides and polysulfides may remain localized near the positive electrode. Some fraction of these discharge products, however, will dissolve in the solvent of the electrolyte and move freely through the liquid containing regions of the cell. As mentioned, some of these dissolved discharge products may actually precipitate from solution and become unavailable for further electrochemical reaction, thereby reducing the cell's capacity. The present invention addresses this problem.

In one preferred embodiment, the materials for the negative electrodes include a metal such lithium or sodium or an alloy of one of these with one or more additional alkali metals and/or alkaline earth metals. Preferred alloys include lithium aluminum alloys, lithium silicon alloys, lithium tin alloys, and sodium lead alloys (e.g., $Na_4Pb$). Other metallic electrodes may include alkaline earth electrodes such as magnesium and their alloys; transition metal electrodes such as aluminum, zinc, and lead and their alloys;

The surface of such metallic negative electrodes can be modified to include a protective layer on the electrolyte side. This protective layer should be conductive to lithium ions and help prevent the formation of lithium dendrites or "mossy" lithium on repeated cycling. It can be produced by the action of additives, including organosulfur compounds, phosphates, iodides, nitrides, and fluorides. The protective layer may also be pre-formed from an inert physical barrier conductive to the metal ions from the negative electrode. Examples of such pre-formed protective layers include lithium phosphate, silicate glasses, polymers, or a combinations of these. In a particularly preferred embodiment, the protective layer is poly(I-trimethylsilyl-1-propyne) ("PTMSP"). The protected negative electrodes may not require an electrolyte separator, thereby allowing the thin film cells of this invention to be made even thinner.

In an alternative embodiment, the negative electrode may be an intercalation electrode such as a carbon-based lithium ion electrode. Such electrodes are available in commercial lithium ion batteries available from Sony Corporation of Japan. These materials are described by Jeffrey Dahn in Chapter I of "Lithium Batteries, New Materials, Developments and Perspectives," edited by G. Pistoia and published by Elsevier (1994), which reference is incorporated herein by reference. Generally, such electrodes have the formula $Li_yC_6$ (where y=0.3 to 2). For many of these materials, the fully charged electrode has the formula $LiC_6$. The intercalation electrode matrix may include graphite, petroleum coke, carbon inserted within highly disordered carbons, etc. The inserted carbon may also be doped with boron, phosphorus, or other appropriate dopant. In one example, the carbon may be prepared from low temperature pyrolysis (about 750° C.) of carbon or carbon-silicon containing polymers such that the carbon product retains some hydrogen or silicon or both. (See, Sato et al., "A Mechanism of Lithium Storage in Disordered Carbons," Science. 264: 556 (22 April 1994), which discusses very good results with a preferred negative electrode of Li inserted within poly p-phenylene-based carbon).

Glass matrix negative electrodes such as $Li/Sn_2O_3$ and $Li/SiO_2$ may also be employed in the batteries of the present invention. These electrodes are similar to the above-described carbon-based intercalation electrodes in that lithium ions are inserted therein during charge and removed during discharge. Such glass matrix electrodes are described in various references including Tahara et al., European Patent Application No. 93111938.2 (1993), Idota et al. Canadian Patent Application, 21134053 (1994), and I. Courtney et al. Meeting Abstacts of the Electrochemical Society, Fall Meeting. San Antonio, Tex., Oct. 6–11, 1996 Vol. 96-2, Abstract # 66, page 88, each of which is incorporated herein by reference for all purposes.

Utilization

In many cases, the battery cells of this invention are rechargeable or secondary cells. Unlike primary cells which discharge only once, the secondary cells of this invention cycle between discharge and charge at least two times. Typically, secondary cells of this invention will cycle at least 50 times, with each cycle having a sulfur utilization (measured as a fraction of 1675 mAh/g sulfur output during the discharge phase of the cycle) of at least about 10%. More preferably, at least 50 cycles will have a minimum sulfur utilization of at least about 20% (most preferably at least about 30%). Alternatively, the secondary cells of this invention will cycle at least two times, with each cycle attaining at least 50% utilization of sulfur in the positive electrode.

As used herein, "utilization" assumes that if all elemental sulfur in an electrode is fully utilized, the electrode will produce 1675 mAh/g of sulfur. That is, 100% utilization corresponds to 1675 mAh/g of the sulfur in the cell, and 10% utilization corresponds to 167.5 mAh/g of sulfur in the cell.

As mentioned, one of the benefits of using the electrolytes of this invention with lithium-sulfur cells is that they keep relatively insoluble sulfide and polysulfide discharge products in "circulation." The thin film cell geometries of this invention also serve the same purpose. This allows the capacity of the cell to remain high after repeated cycles.

It should be understood that using the electrolytes of this invention which solubilize sulfur discharge products to a great extent, "self-discharge" must be considered. That is, because the discharge products of the positive electrode are quite soluble in the electrolytes of this invention, they will automatically dissolve from the positive electrode and move to the negative electrode where they could be reduced chemically without producing electrical energy. Obviously, such self-discharged mechanism is to be avoided. One way of mitigating this effect is by providing a protective layer on the negative electrode which prevents these dissolved discharge products from reaching the negative electrode and thereby reacting with it. As mentioned above, such protective layers will generally conduct metal ions but not allow most other species from reaching the negative electrode. Again, examples of protective layers include lithium phosphate, silicate glasses, polymers, or a combinations of these.

EXAMPLES

Various experiments were conducted to demonstrate the performance advantages provided by the various aspects of this invention. The results of a few such experiments are tabulated in FIG. 4. It should be understood that the experiments described herein represent but a small sampling of all experiments on lithium-sulfur liquid systems conducted by or under the direction of the inventors. The experiments are provided mainly to show the high level of performance that can be attained when following the guidelines presented herein.

Example 1

A cathode film was made by mixing 50 (wt) % elemental sulfur, 24% carbon black, 18% polyethylene oxide Mw=900 k (PEO), 2% Brij, and 6% lithium-trifluoromethanesulfonimide, in a solution of acetonitrile (solvent to solids ratio, 20:1 by weight). The components were stir-mixed for approximately two days until the slurry is well mixed and uniform. Thin cathode film were cast directly onto stainless steel current collectors, and the solvent was allowed to evaporate at ambient temperatures. The resulting cathode film weighed approximately 0.0015 gm per $cm^2$.

The separator was a micro-porous polymeric sheet having a nominal thickness of 1 mil (Hoechst Celanese, Celgard 2400). The cathode film and microporous separator were vacuum dried overnight to remove moisture prior to transfer into the argon glovebox for final cell assembly.

65 microliter of the electrolyte, which was a 0.5 molar solution of lithium-trifluoromethanesulfonimide (3M Company of Charlotte, N.C.) in tetraglyme, was placed on the cathode film followed by placement of the microporous separator on the cathode. An additional 90 microliter of electrolyte was then placed on the micro-porous separator. A 5 mil (125 micron) thick high purity lithium anode film (FMC/Lithco of Gastonia, N.C.) was then placed on the other side of the micro-porouse separator sheet.

Figure 5:
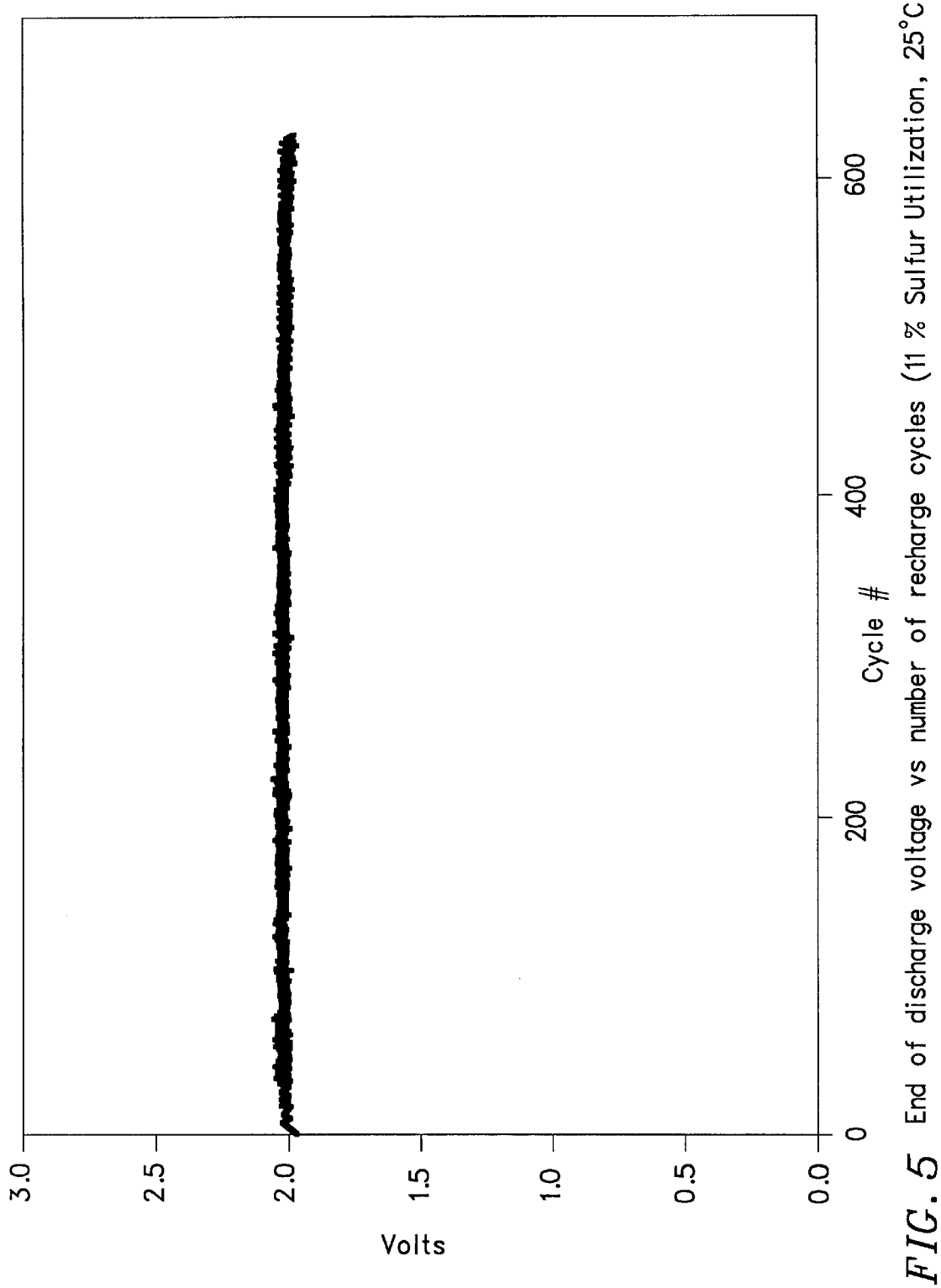
FIG. 5 is a graph of end of discharge voltage after each recharge cycle for the cell described in Example 1.

The cell was then evaluated at 25° C. with a Series 4000 battery test system from Maccor Inc. of Tulsa Okla. This cell was cycled to a constant capacity corresponding to delivering 180 mAh per gm of the sulfur in the cell, that is, a utilization of 11% of the sulfur. The rates used were 90 microamp/cm$^2$ for discharging and 40 microamp/cm$^2$ for charging to cutoff voltages of 1.8 and 3.2 volts, respectively. FIG. 5 shows the end of discharge voltage of this cell after each recharge cycle. As evident from the graph the cell performance is very consistent and over 600 cycles have been obtained.

Example 2

A cathode film was made by impregnating a slurry identical to the one described in example 1 into a carbon fiber paper (Lydall Technical Papers, Rochester, N.Y.), and the solvent was allowed to evaporate at ambient temperatures. (This cathode was a carbon paper impregnated with slurry such that sulfur loading is of type I (see "methods" section)). The resulting cathode film weighed approximately 0.0029 gm per cm$^2$ and was vacuum dried overnight prior to transfer into the argon glovebox for final cell assembly.

135 microliter of the electrolyte of a 0.5 molar solution of lithium-trifluoromethanesulfonimide in tetraglyme was placed on the cathode film followed by placement of the microporous separator on the cathode. The separator was identical to the one described in example 1. An additional 45 microliter of electrolyte was then placed on the other side of the micro-porous separator. A 5 mil (125 micron) thick lithium anode film (FMC/Lithco Gastonia, N.C.) was then placed on the micro-porous separator sheet. Once assembled, the cell was compressed at 2 psi.

Figure 6:
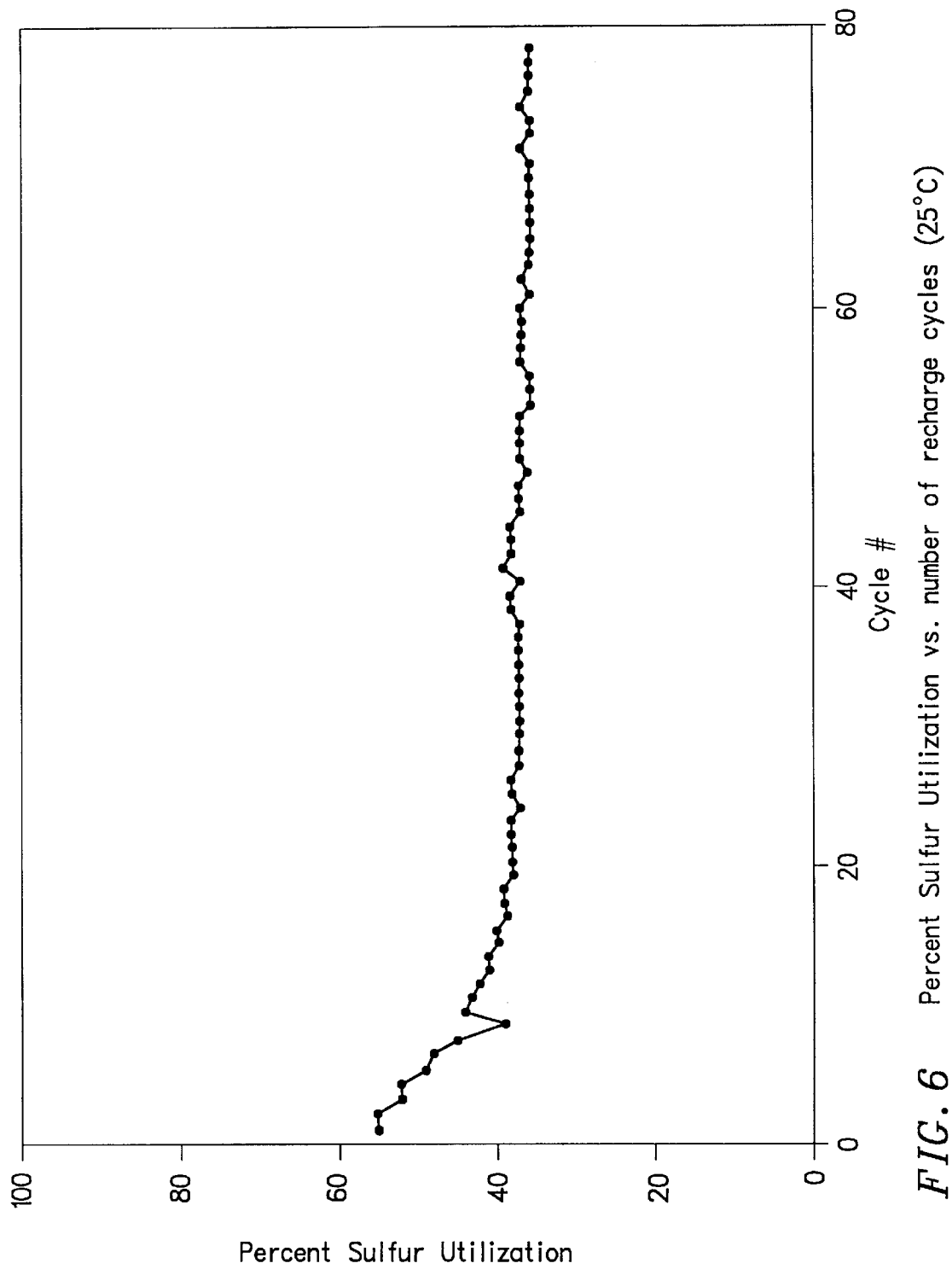
FIG. 6 is a graph of the percent sulfur utilization after each recharge cycle for the cell described in Example 2.

The cell was tested under similar conditions as described in example 1. The rates used were 90 microamp/cm$^2$ for discharging and for recharging. FIG. 6 shows the percent sulfur utilization of this cell after each recharge cycle. As evident from the graph the cell performance is very consistent and more than 70 recharge cycles have been obtained at a sulfur utilization of approximately 40%.

Example 3

A cathode film similar to the one described in example 2 was made with a slurry composition of 70 (wt)% carbon black, 25% polyethylene oxide (PEO, Mw=900 k) and 5% Brij. The resulting cathode film weighed approximately 0.0037 g/cm$^2$ and was vacuum dried overnight prior to transfer into the argon glovebox for final cell assembly. (This cathode was a carbon paper cathode impregnated with slurry; sulfur loading was of type III.)

Sulfur was added to the cathode by inserting 200 microliter of a tetraethylene glycol dimethyl ether solution containing 0.5 moles of lithium-trifluoromethanesulfonimide and approximately 3 moles of sulfur dissolved. After insertion of the dissolved sulfur into the cathode, the microporous separator (identical to the one described in example 1) was placed on the cathode. This was then followed by the placement of an additional 20 microliter of the above mentioned dissolved sulfur solution on the microporous separator. A 5 mil (125 micron) thick lithium anode film (FMC/Lithco Gastonia, N.C.) was then placed on the microporous separator sheet. Once assembled, the cell was compressed at 2 psi.

Figure 7:
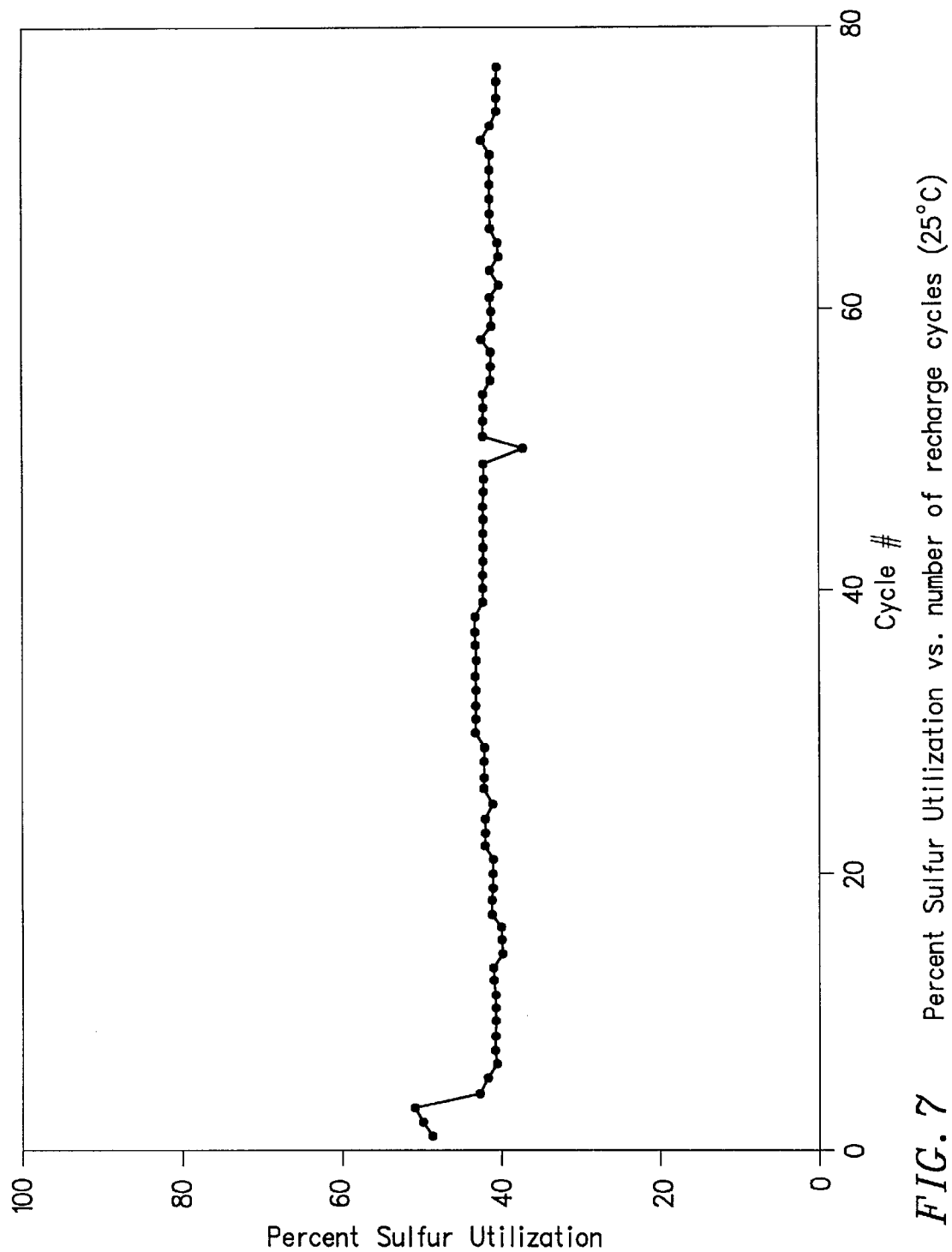
FIG. 7 is a graph of percent sulfur utilization versus cycle number for the cell described in Example 3.

The cell was tested under similar conditions as described in example 1. The rates used were 500 microamp/cm$^2$ for discharging to a cutoff voltage of 1.5 V and 90 microamp/cm$^2$ for recharging. FIG. 7 shows the percent sulfur utilization of this cell after each recharge cycle. As evident from the graph the cell performance is very consistent and more than 70 recharge cycles have been obtained at a sulfur utilization of approximately 40%.

Example 4

Figure 8:
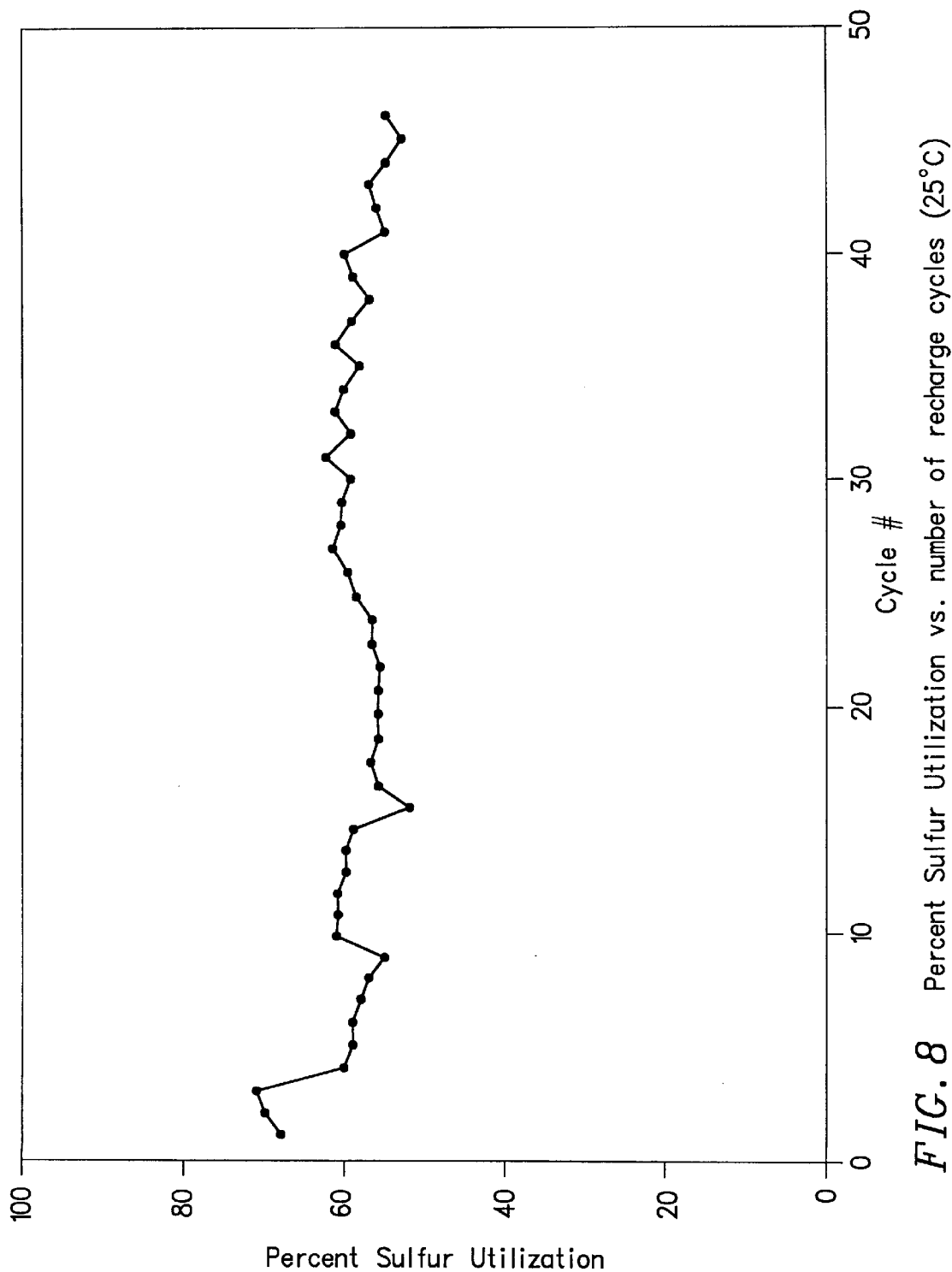
FIG. 8 is a graph of the percent sulfur utilization versus number of recharge cycles for the cell described in Example 4.

A cell identical to the one in example 3 was tested under similar conditions as described in example 1 at a discharge rate of 90 microamp/cm$^2$. FIG. 8 shows that the sulfur utilization of this cell is of approximately 60% for more than 35 recharge cycles.

Example 5

Figure 9:
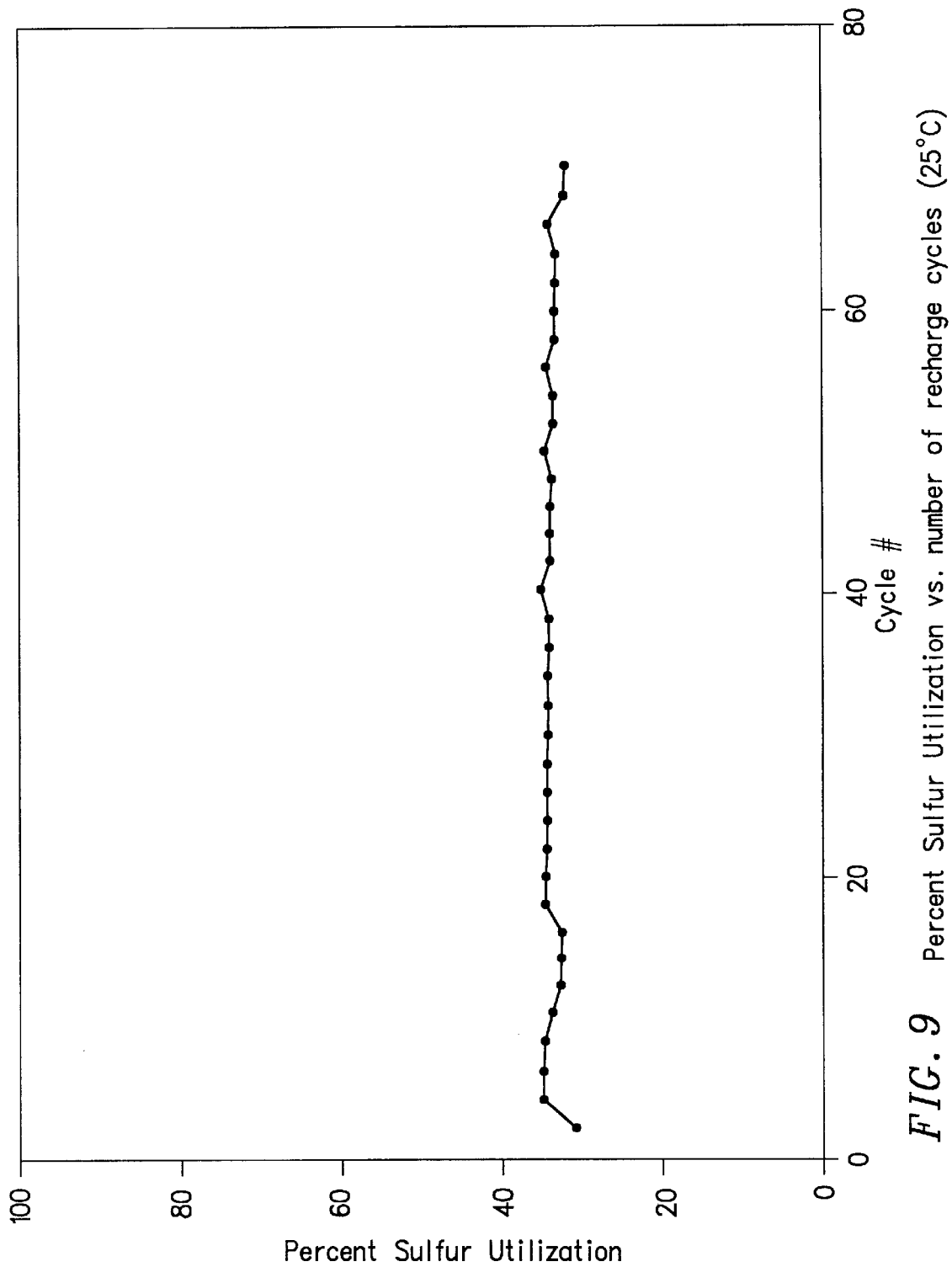
FIG. 9 is a graph of percent sulfur utilization versus number or recharge cycles for the cell described in Example 5.
Figure 10:
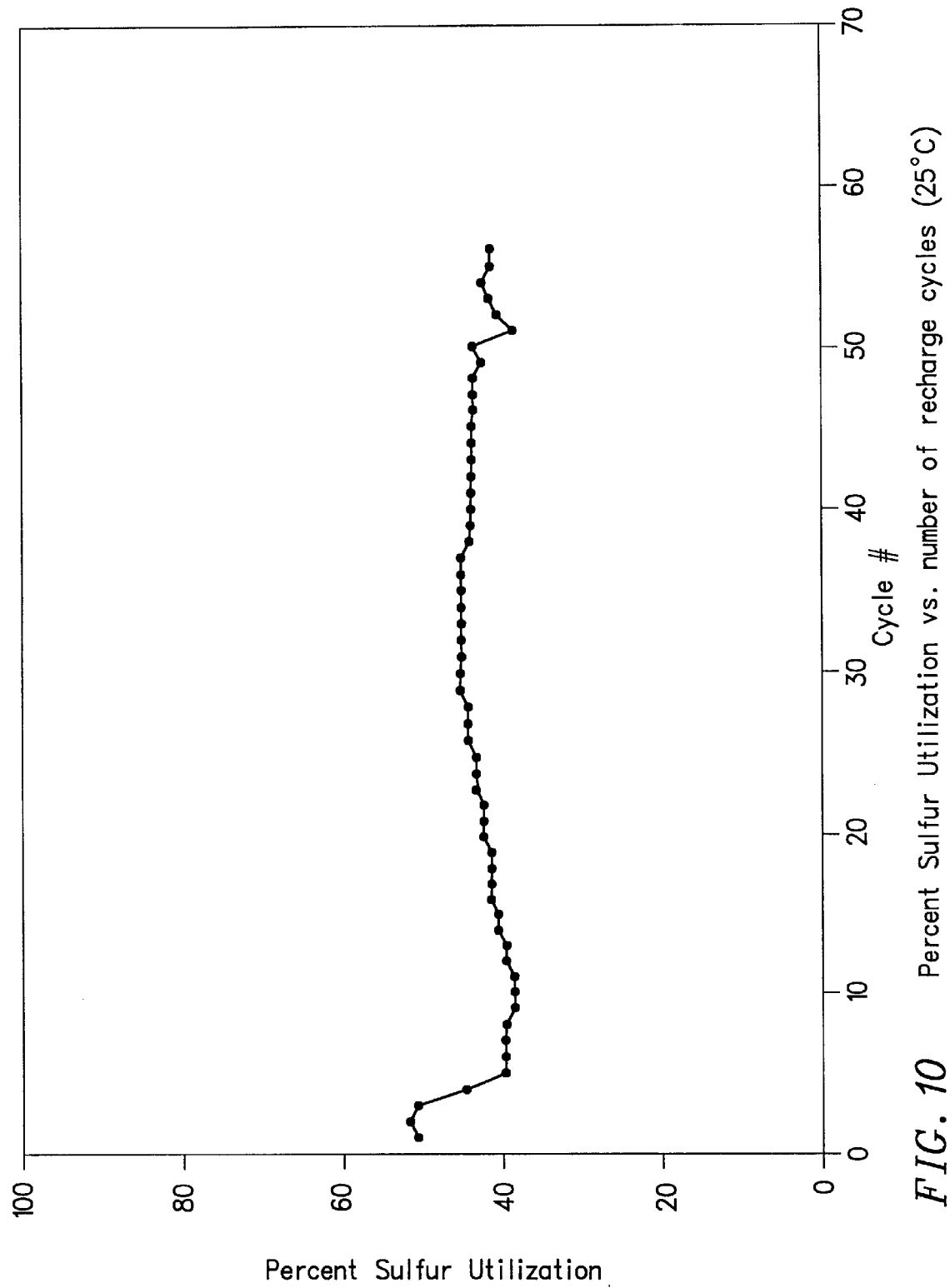
FIG. 10 is a graph of percent sulfur utilization versus number or recharge cycles for the cell described in Example 6.

A cell similar to the one described in example 3, but having a cathode weight of 0.00197 gm/cm$^2$ and 230 microliters of the dissolved sulfur solution (identical to the sulfur solution described in example 3) impregnated into the cathode, was tested under similar conditions as described in example 1. The rates used were 1000 microamp/cm$^2$ for discharging to a cutoff voltage of 1.5 V and 500 microamp/cm$^2$ for recharging. The total volume of catholyte added to the cell was 250 microliters. As evident from FIG. 9 the cell performance is very consistent and more than 30 recharge cycles have been obtained at a sulfur utilization of approximately 30%.

Example 6

A cathode film similar to the one described in example 3 was made with a slurry composition of 80 (wt) % carbon black, and 20% by solids content weight of a teflon dispersion (DuPont Company of Wilmington, Del.). (The cathode is similar to the one in example 3, except the cathode components are active sulfur, Teflon binder and carbon black, in this example there is no solid state ionic conductor or gelled ionic conductor. The sulfur loading is of Type III.) The resulting cathode film weighed approximately 0.0039 g/cm$^2$ and was vacuum dried overnight prior to transfer into the argon glovebox for final cell assembly.

Other Embodiments

The foregoing describes the instant invention and its presently preferred embodiments. Numerous modifications and variations in the practice of this invention are expected to occur to those skilled in the art. For example, the invention may provide overcharge protection as described in U.S. patent application Ser. No. 08/686,609, filed Jul. 26, 1996, and entitled RECHARGEABLE POSITIVE ELECTRODES and U.S. patent application Ser. No. 08/782,245, filed Mar. 19, 1997, and entitled OVERCHARGE PROTECTION SYSTEMS FOR RECHARGEABLE BATTERIES. Such modifications and variations are encompassed within the following claims.

All references cited herein are incorporated by reference for all purposes.

What is claimed is:

1. A battery cell comprising:

a) a negative electrode including a metal or an ion of the metal;

b) a positive electrode comprising a mixture of
   i) an electrochemically active material comprising sulfur in the form of at least one of elemental sulfur, a sulfide of the metal, and a polysulfide of the metal, and
   ii) an electronically conductive material; and
c) a liquid electrolyte including a
   i) main solvent having the chemical formula $R_1(CH_2CH_2O)_nR_2$, where n ranges between 2 and 10, $R_1$ and $R_2$ are different or identical groups selected from the group consisting of alkyl, alkoxy, substituted alkyl, and substituted alkoxy groups; and
   ii) a cosolvent having a donor number of at least about 15.

2. The battery cell of claim 1, wherein at least about 10% of the sulfur in the positive electrode is utilized in at least 50 cycles, wherein 100% utilization corresponds to 1675 mAh/g of the sulfur in the battery cell.

3. The battery cell of claim 2, wherein at least about 20% of the sulfur in the positive electrode is utilized in at least 50 successive cycles, wherein 100% utilization corresponds to 1675 mAh/g of the sulfur in the positive electrode.

4. The battery cell of claim 1, wherein the solvent is a polyglyme of the chemical formula $CH_3O(CH_2CH_2O)_nCH_3$.

5. The battery cell of claim 4, wherein the solvent is tetraglyme, $CH_3O(CH_2CH_2O)_4CH_3$.

6. The battery cell of claim 1, wherein $R_1$ and $R_2$ together with $(CH_2CH_2O)_n$ form a closed ring.

7. The battery cell of claim 1, wherein the donor solvent is present in a concentration of at least about 10% by volume.

8. The battery cell of claim 1, wherein the donor solvent is at least one of hexamethylphosphoramide, pyridine, N,N-diethylacetamide, N,N-diethylformamide, dimethylsulfoxide, tetramethylurea, N,N-dimethylacetamide, N,N-dimethylformamide, tributylphosphate, trimethylphosphate N,N,N',N'-tetraethylsulfamide, tetramethylenediamine, tetramethylpropylenediamine, and pentamethyldiethylenetriamine.

9. The battery cell of claim 1, wherein the electrolyte solvent comprises an acceptor solvent.

10. The battery cell of claim 9, wherein the acceptor solvent is at least one of methanol, ethylene glycol, polyethylene glycol, nitromethane, trifluoroacetic acid, trifluoromethanesulfonic acid, sulfur dioxide, and boron trifluoride.

11. The battery cell of claim 1, wherein the metal in the negative electrode is at least one of sodium and lithium.

12. The battery cell of claim 11, wherein the metal in the negative electrode is lithium.

13. The battery cell of claim 1, wherein the negative electrode is a lithium intercalation electrode.

14. The battery cell of claim 1, wherein the electronic conductor of the positive electrode is at least one of carbon and an electronically conductive polymer.

15. A battery cell comprising:
a) a negative electrode including a metal or an ion of the metal;
b) a positive electrode comprising a mixture of
   i) an electrochemically active material comprising sulfur in the form of at least one of elemental sulfur, a sulfide of the metal, and a polysulfide of the metal, and
   ii) an electronically conductive material; and
c) a liquid electrolyte including a solvent having at least one of a crown ether and a cryptand, and a donor solvent.

16. The battery cell of claim 15, wherein at least about 10% of the sulfur in the positive electrode is utilized in at least 50 cycles, wherein 100% utilization corresponds to 1675 mAh/g of the sulfur in the battery cell.

17. The battery cell of claim 16, wherein at least about 20% of the sulfur in the positive electrode is utilized in at least 50 successive cycles, wherein 100% utilization corresponds to 1675 mAh/g of the sulfur in the positive electrode.

18. The battery cell of claim 15, wherein the solvent is a crown ether.

19. The battery cell of claim 18, wherein the crown ether is at least one of 18-crown-6, 15-crown-5, dibenzo-18-crown-6, and 12-crown-4.

20. The battery cell of claim 15, wherein the solvent is a cryptand.

21. The battery cell of claim 15, wherein the donor solvent is at least one of hexamethylphosphoramide, pyridine, N,N-diethylacetamide, N,N-diethylformamide, dimethylsulfoxide, tetramethylurea, N,N-dimethylacetamide, N,N-dimethylformamide, tributylphosphate, trimethylphosphate, N,N,N',N'-tetraethylsulfamide, tetramethylenediamine, tetramethylpropylenediamine, and pentamethyldiethylenetriamine.

22. The battery cell of claim 15, wherein the electrolyte further comprises an acceptor solvent.

23. The battery cell of claim 22, wherein the acceptor solvent is at least one of methanol, ethylene glycol, polyethylene glycol, nitromethane, trifluoroacetic acid, trifluoromethanesulfonic acid, sulfur dioxide, and boron trifluoride.

24. The battery cell of claim 15, wherein the metal in the negative electrode is at least one of sodium and lithium.

25. The battery cell of claim 24, wherein the metal in the negative electrode is lithium.

26. The battery cell of claim 15, wherein the negative electrode is a lithium intercalation electrode.

27. The battery cell of claim 15, wherein the electronic conductor of the positive electrode is at least one of carbon and an electronically conductive polymer.

28. A rechargeable battery cell comprising:
a) a negative electrode including a metal or an ion of the metal;
b) a positive electrode comprising a mixture of
   an electrochemically active material comprising sulfur in the form of at least one of elemental sulfur, a sulfide of the metal, and a polysulfide of the metal, and
   an electronically conductive material; and
c) a liquid electrolyte including a solvent for at least some discharge products of the positive electrode,
   wherein the rechargeable battery cell is characterized by at least one of the following criteria:
   i) the battery cell attains at least about 10% utilization over at least fifty cycles, and
   ii) the battery cell attains at least about 50% utilization over two or more cycles.

29. The battery cell of claim 28, wherein the battery cell attains at least about 30% utilization over at least fifty cycles.

30. The battery cell of claim 28, wherein the battery cell attains at least about 50% utilization over at least 10 cycles.

31. The battery cell of claim 28, wherein the battery cell attains at least about 50% utilization over at least 75 cycles.

32. The battery cell of claim 28, wherein the metal and a negative electrode is at least one of sodium and lithium.

33. The battery cell of claim 28, wherein the negative electrode is a lithium intercalation electrode.

34. The battery cell of claim 28, wherein the electronic conductor of the positive electrode is at least one of carbon and an electronically conductive polymer.

35. The battery cell of claim 28, wherein the liquid electrolyte solvent has the chemical formula $R_1(CH_2CH_2O)_nR_2$, wherein n ranges between 2 and 10, $R_1$, and $R_2$, are different or identical groups selected from the group consisting of alkyl, alkoxy, substituted alkyl, and substituted alkoxy groups.

36. The battery cell of claim 33, wherein $R_1$ and $R_2$ together with $(CH_2CH_2O)_n$ form a closed ring.

37. The battery cell of claim 33, wherein the electrolyte further comprises a donor solvent.

38. The battery cell of claim 28, wherein the battery cell is characterized by a separation distanced between a back boundary where a catholyte is farthest removed from the negative electrode and a front boundary where the catholyte is nearest the negative electrode, wherein the separation distance is not greater than about 400 micrometers.

39. The battery cell of claim 28, wherein the electronically conductive material comprises an interconnected matrix.

40. The battery cell of claim 28, wherein the cell discharges at an average current density of at least about 0.5 mA/cm$^2$ over at least 50 cycles in criteria (i) and at least 2 cycles in criteria (ii).

41. A battery cell comprising:
    a) a negative electrode including a metal or an ion of the metal;
    b) a positive electrode comprising a mixture of
        i) an electrochemically active material comprising sulfur in the form of at least one of elemental sulfur, a sulfide of the metal, and a polysulfide of the metal, and
        ii) an electronically conductive material; and
    c) a liquid electrolyte defining a catholyte of the solvent and dissolved discharged products from the positive electrode,
        wherein the battery cell is characterized by a separation distanced between a back boundary where the catholyte is farthest removed from the negative electrode and a front boundary where the catholyte is nearest the negative electrode,
        wherein the separation distance is not greater than about 400 micrometers.

42. The battery cell of claim 41, wherein the separation distance is not greater than about 300 micrometers.

43. The battery cell of claim 41, wherein the battery cell comprises two positive electrodes with the negative electrode disposed therebetween.

44. The battery cell of claim 41, wherein electronically conductive material comprises an interconnected matrix.

45. The battery cell of claim 41, wherein the positive electrode is disposed on positive current collector.

46. The battery cell of claim 41, wherein the catholyte concentration is between about 3 and 30 moles of sulfur per liter.

47. The battery cell of claim 46, wherein the catholyte concentration is between about 7 and 25 mole of sulfur per liter.

48. The battery cell of claim 47, wherein the catholyte to concentration is between about 10 and 20 moles of sulfur per liter.

49. The battery cell of claim 41, wherein the separation distance is not greater than about 150 micrometers.

* * * * *